（12）United States Patent
Genosar et al.

(10) Patent No.: US 8,663,188 B2
(45) Date of Patent: Mar. 4, 2014

(54) DISPENSER AND THERAPEUTIC PACKAGE SUITABLE FOR ADMINISTERING A THERAPEUTIC SUBSTANCE TO A SUBJECT, ALONG WITH METHOD RELATING TO SAME

(75) Inventors: Amir Genosar, Boulder, CO (US); Romi Genosar, Boulder, CO (US)

(73) Assignee: Aktivpak, Inc., Boulder, CO (US)

( * ) Notice: Subject to any disclaimer, the term of this patent is extended or adjusted under 35 U.S.C. 154(b) by 840 days.

(21) Appl. No.: 12/344,044

(22) Filed: Dec. 24, 2008

(65) Prior Publication Data

US 2009/0171311 A1    Jul. 2, 2009

Related U.S. Application Data

(60) Provisional application No. 61/017,365, filed on Dec. 28, 2007.

(51) Int. Cl.
*A61M 5/32* (2006.01)

(52) U.S. Cl.
USPC ............................................ 604/411; 222/95

(58) Field of Classification Search
USPC .............. 604/403, 410–415; 222/92, 95, 163, 222/206, 213, 214
See application file for complete search history.

(56) References Cited

U.S. PATENT DOCUMENTS

| 2,743,724 A | 5/1956 | Gispen |
| 2,794,437 A | 6/1957 | Tash |
| 3,074,544 A | 1/1963 | Bollmeier et al. |
| 3,315,801 A | 4/1967 | Lowry |
| 3,387,609 A | 6/1968 | Shields |
| 3,521,805 A | 7/1970 | Ward |
| 3,554,256 A | 1/1971 | Anderson |
| 3,608,709 A | 9/1971 | Pike |
| 3,635,376 A | 1/1972 | Hellstrom |
| 3,741,384 A | 6/1973 | Cloud |
| 3,749,620 A | 7/1973 | Montgomery |
| 3,847,279 A | 11/1974 | Montgomery |
| 3,946,732 A | 3/1976 | Hurscham |
| 3,968,872 A | 7/1976 | Cavazza |
| 3,986,640 A | 10/1976 | Redmond |
| 4,011,949 A | 3/1977 | Braber et al. |

(Continued)

FOREIGN PATENT DOCUMENTS

| DE | 26 47 166 | 5/1977 |
| DE | 27 51 078 | 5/1979 |

(Continued)

OTHER PUBLICATIONS

Documents printed from www.rommelag.com, 4 pages printed on Jan. 25, 2010.
Documents printed from www.weiler-bfs.com, 10 pages printed on Jan. 25, 2010.
Documents printed from www.sarong.it, 7 pages printed on Jan. 25, 2010.

(Continued)

*Primary Examiner* — Melanie Hand
(74) *Attorney, Agent, or Firm* — Perkins Coie LLP

(57) ABSTRACT

A dispensing device comprises a sealed package including a collapsible compartment and an administration assembly. The administration assembly includes a delivery device in fluid communication with a substance within the sealed package. A compression panel collapses the compartment to dispense a substance through the delivery device. Embodiments for a single use dispenser for hypodermic administration of a unit dose of a therapeutic fluid, as well as therapeutic packages and methods for administering therapeutic substances to subjects, are also provided.

16 Claims, 18 Drawing Sheets

(56) References Cited

U.S. PATENT DOCUMENTS

| | | | |
|---|---|---|---|
| 4,020,836 A | 5/1977 | Cunningham |
| 4,051,851 A | 10/1977 | Tischlinger |
| 4,072,149 A | 2/1978 | Tischlinger |
| 4,078,565 A | 3/1978 | Genese |
| 4,084,588 A | 4/1978 | Koenig |
| 4,084,718 A | 4/1978 | Wadsworth |
| 4,140,409 A | 2/1979 | DeVries |
| 4,236,652 A | 12/1980 | Beguhn |
| 4,411,659 A * | 10/1983 | Jensen et al. ........... 604/332 |
| 4,430,013 A | 2/1984 | Kaufman |
| 4,441,659 A | 4/1984 | Marklund |
| 4,479,989 A | 10/1984 | Mahal |
| 4,493,574 A | 1/1985 | Redmond et al. |
| 4,548,601 A | 10/1985 | Lary |
| 4,602,910 A | 7/1986 | Larkin |
| 4,608,043 A | 8/1986 | Larkin |
| 4,611,715 A | 9/1986 | Redmond |
| 4,648,506 A | 3/1987 | Campbell |
| 4,691,495 A | 9/1987 | Schuh |
| 4,724,982 A | 2/1988 | Redmond |
| 4,819,406 A | 4/1989 | Redmond |
| 4,871,091 A | 10/1989 | Preziosi |
| 4,955,871 A | 9/1990 | Thomas |
| 4,961,495 A | 10/1990 | Yoshida et al. |
| 5,029,718 A | 7/1991 | Rizzardi |
| 5,131,760 A | 7/1992 | Farmer |
| 5,176,634 A * | 1/1993 | Smith et al. ........... 604/87 |
| 5,241,150 A | 8/1993 | Garvey et al. |
| 5,287,961 A | 2/1994 | Herran |
| 5,316,400 A | 5/1994 | Hoyt et al. |
| 5,368,199 A | 11/1994 | Haas et al. |
| 5,383,851 A | 1/1995 | McKinnon, Jr. et al. |
| 5,395,031 A | 3/1995 | Redmond |
| 5,425,447 A | 6/1995 | Farina |
| 5,462,526 A | 10/1995 | Barney et al. |
| 5,478,337 A * | 12/1995 | Okamoto et al. ........... 604/413 |
| 5,533,412 A | 7/1996 | Jerman et al. |
| 5,543,097 A | 8/1996 | Fang |
| 5,616,132 A | 4/1997 | Newman |
| 5,637,087 A | 6/1997 | O'Neil et al. |
| 5,681,291 A | 10/1997 | Galli |
| 5,687,550 A | 11/1997 | Hansen et al. |
| 5,716,343 A | 2/1998 | Kriesel et al. |
| 5,836,922 A | 11/1998 | Hansen et al. |
| RE35,986 E | 12/1998 | Ritson et al. |
| 5,848,991 A | 12/1998 | Gross et al. |
| 5,884,759 A | 3/1999 | Gueret |
| 5,921,962 A | 7/1999 | Kriesel et al. |
| 5,957,895 A | 9/1999 | Sage et al. |
| 6,007,264 A | 12/1999 | Koptis |
| 6,017,598 A | 1/2000 | Kreischer et al. |
| 6,041,930 A | 3/2000 | Cockburn |
| 6,045,534 A | 4/2000 | Jacobsen et al. |
| 6,085,942 A | 7/2000 | Redmond |
| 6,086,562 A | 7/2000 | Jacobsen et al. |
| 6,148,996 A | 11/2000 | Morini |
| 6,171,285 B1 * | 1/2001 | Johnson ........... 604/195 |
| 6,203,535 B1 | 3/2001 | Barney et al. |
| 6,245,056 B1 | 6/2001 | Walker et al. |
| 6,258,063 B1 | 7/2001 | Haar et al. |
| 6,354,603 B1 | 3/2002 | Villette |
| 6,435,341 B1 | 8/2002 | Nobbio |
| 6,530,900 B1 | 3/2003 | Daily et al. |
| 6,656,147 B1 | 12/2003 | Gertsek et al. |
| 6,675,660 B1 | 1/2004 | Mosier et al. |
| 6,743,211 B1 | 6/2004 | Prausnitz et al. |
| 6,780,171 B2 | 8/2004 | Gabel et al. |
| 6,781,171 B2 | 8/2004 | Jang et al. |
| 6,805,998 B2 | 10/2004 | Jenson et al. |
| 6,906,436 B2 | 6/2005 | Jenson et al. |
| 6,924,164 B2 | 8/2005 | Jenson |
| 6,979,316 B1 * | 12/2005 | Rubin et al. ........... 604/156 |
| 6,996,951 B2 | 2/2006 | Smith et al. |
| 7,004,213 B2 | 2/2006 | Hansen |
| 7,011,650 B2 | 3/2006 | Rosoff et al. |
| 7,025,200 B2 | 4/2006 | Fontana |
| 7,115,108 B2 | 10/2006 | Wilkinson et al. |
| 7,121,409 B1 | 10/2006 | Hamilton et al. |
| 7,192,549 B2 | 3/2007 | Hansen |
| 7,225,683 B2 | 6/2007 | Harnett et al. |
| 7,407,493 B2 | 8/2008 | Cane |
| 7,416,540 B2 | 8/2008 | Edwards et al. |
| 7,464,811 B2 | 12/2008 | Patterson et al. |
| 2001/0047162 A1 | 11/2001 | Yugari |
| 2002/0123740 A1 | 9/2002 | Flaherty et al. |
| 2003/0080129 A1 | 5/2003 | Takimoto et al. |
| 2004/0240324 A1 | 12/2004 | Isbitsky et al. |
| 2004/0249339 A1 | 12/2004 | Willis et al. |
| 2005/0004514 A1 | 1/2005 | Hochman |
| 2006/0079862 A1 | 4/2006 | Genosar |
| 2006/0276755 A1 | 12/2006 | Sullivan et al. |
| 2006/0283727 A1 | 12/2006 | Nelson et al. |
| 2007/0144923 A1 * | 6/2007 | Houwaert et al. ........... 206/219 |
| 2007/0299391 A1 * | 12/2007 | Yoshikawa et al. ........... 604/82 |
| 2008/0177244 A1 * | 7/2008 | Capitaine et al. ........... 604/414 |
| 2008/0249499 A1 | 10/2008 | Vancaillie et al. |
| 2008/0300570 A1 | 12/2008 | Fowles et al. |
| 2010/0179473 A1 | 7/2010 | Genosar |

FOREIGN PATENT DOCUMENTS

| | | |
|---|---|---|
| DE | 42 03 430 | 8/1993 |
| DE | 100 32 937 A1 | 1/2001 |
| EP | 0 088 730 | 9/1983 |
| EP | 0 088 731 | 9/1983 |
| EP | 0370571 B1 | 10/1993 |
| EP | 1201233 | 5/2002 |
| FR | 1.065.305 | 5/1954 |
| FR | 1121237 A | 7/1956 |
| FR | 2633519 A1 | 1/1990 |
| GB | 697643 | 9/1953 |
| GB | 770341 A | 3/1957 |
| WO | WO 92/20595 | 11/1992 |
| WO | WO 97/06073 | 2/1997 |
| WO | WO 01/78806 | 10/2001 |
| WO | 02/05889 A1 | 1/2002 |
| WO | 2005/002649 A1 | 1/2005 |
| WO | WO 2007/068032 | 6/2007 |

OTHER PUBLICATIONS

Documents printed from www.lameplast.it, 15 pages printed on Jan. 25, 2010.
Documents printed from www.sanner.de, 5 pages printed on Jan. 25, 2010.
Documents printed from www.justformen.com, 1 page printed on Jan. 27, 2010.
Documents printed from www.unifill.it, 14 pages printed on Jan. 28, 2010.
Documents printed from www.bioject.com, 6 pages printed on Jan. 28, 2010.
Documents printed from www.injex.com, 6 pages printed on Jan. 28, 2010.
Documents printed from www.mediject.com, 2 pages printed on Jan. 28, 2010.
Documents printed from www.zogenix.com, 2 pages printed on Jan. 28, 2010.
Documents printed from www.valeritas.com, 1 page printed on Jan. 28, 2010.
International Searching Authority "Notification of Transmittal of the International Search Report and the Written Opinion of the International Searching Authority, or the Declaration" Mar. 10, 2009.
International Searching Authority "International Search Report and the Written Opinion of the International Searching Authority" for PCT/US07/88918 mailed Aug. 29, 2008.
International Searching Authority "International Preliminary Report on Patentability" for PCT/US07/88918 mailed Jun. 30, 2009.
www.crossject.com.
www.penjet.com.

* cited by examiner

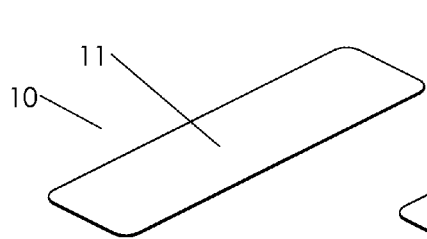
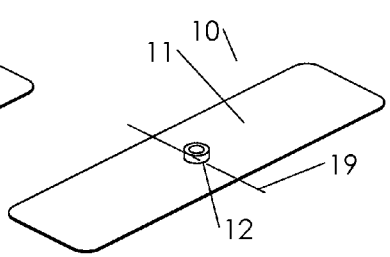
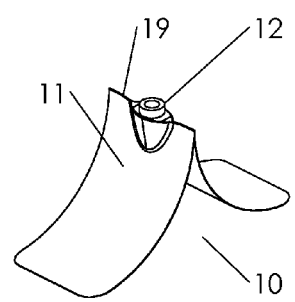
Figure 1a	Figure 1b	Figure 1c
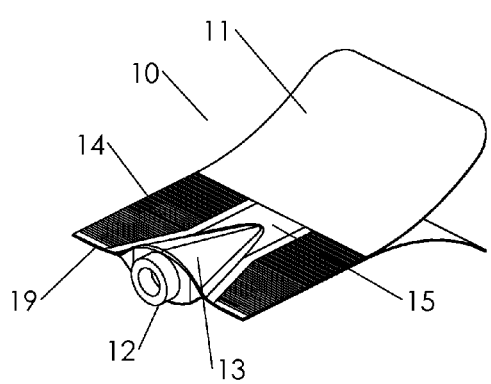
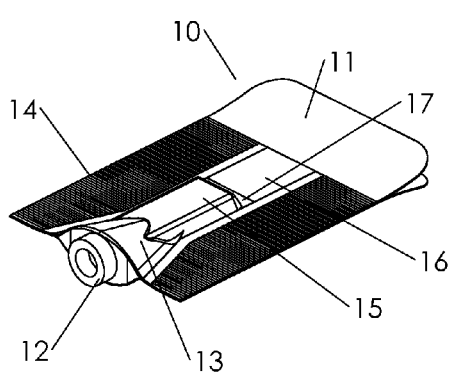
Figure 1d	Figure 1e
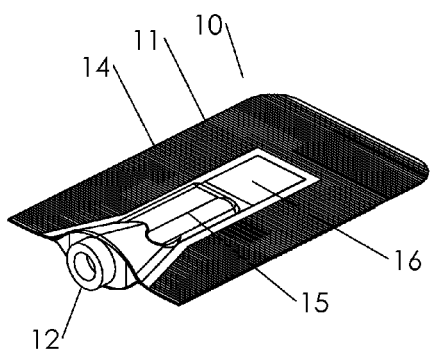
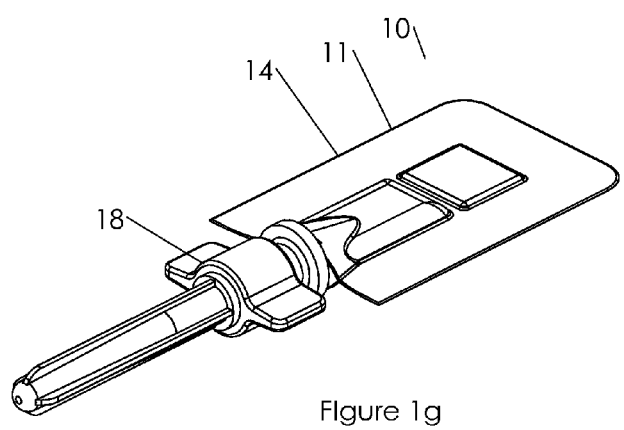
Figure 1f	Figure 1g

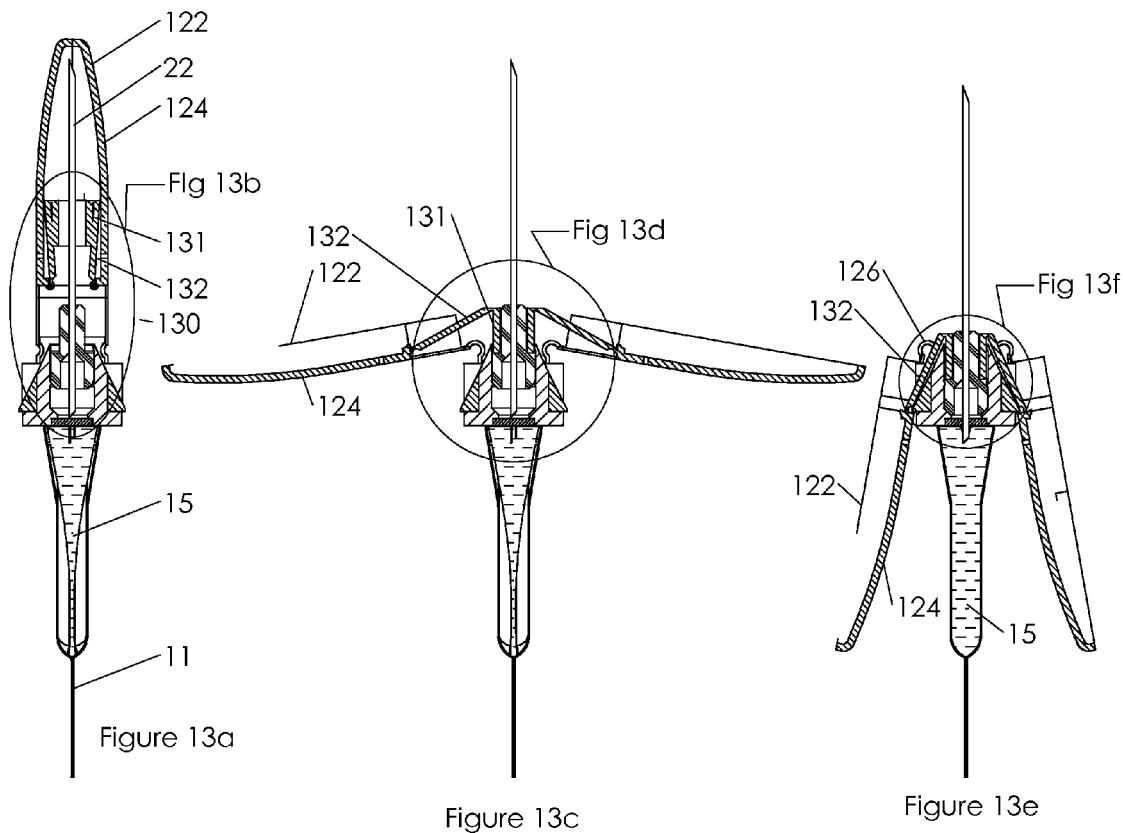
Figure 13a
Figure 13c
Figure 13e
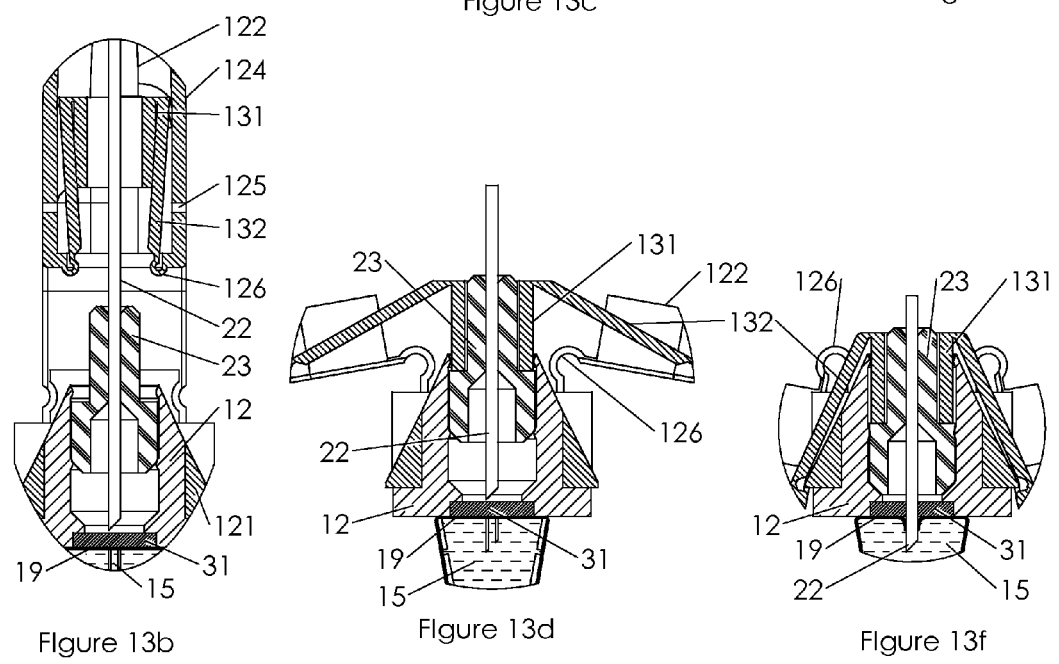
Figure 13b
Figure 13d
Figure 13f

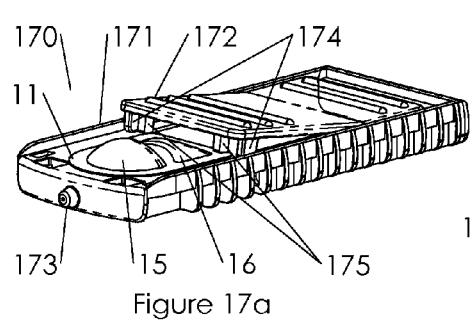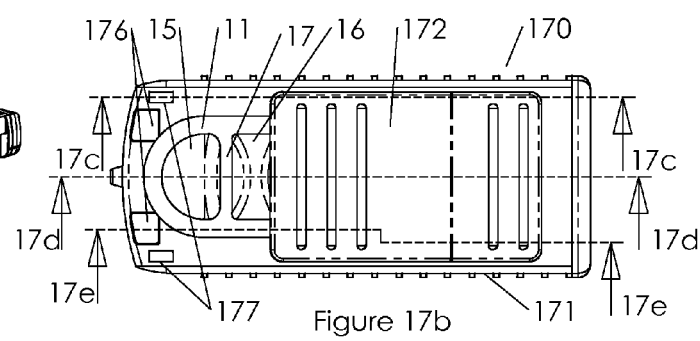
Figure 17a    Figure 17b
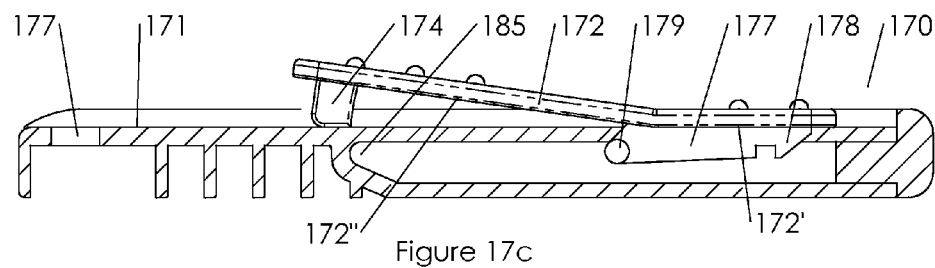
Figure 17c
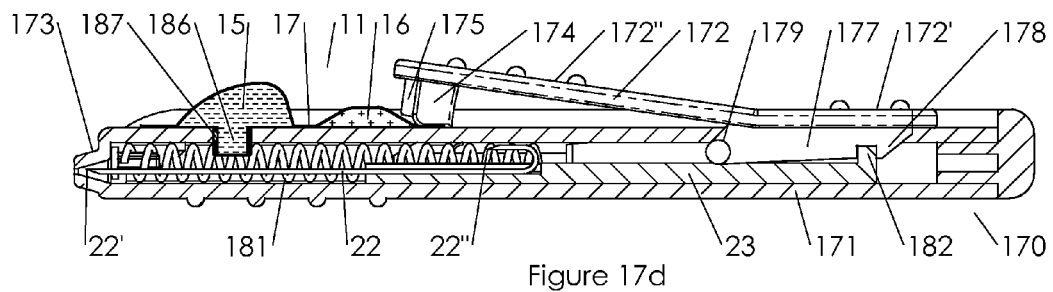
Figure 17d
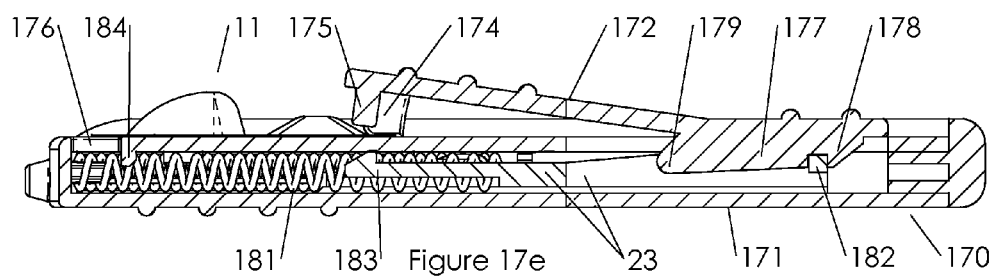
Figure 17e

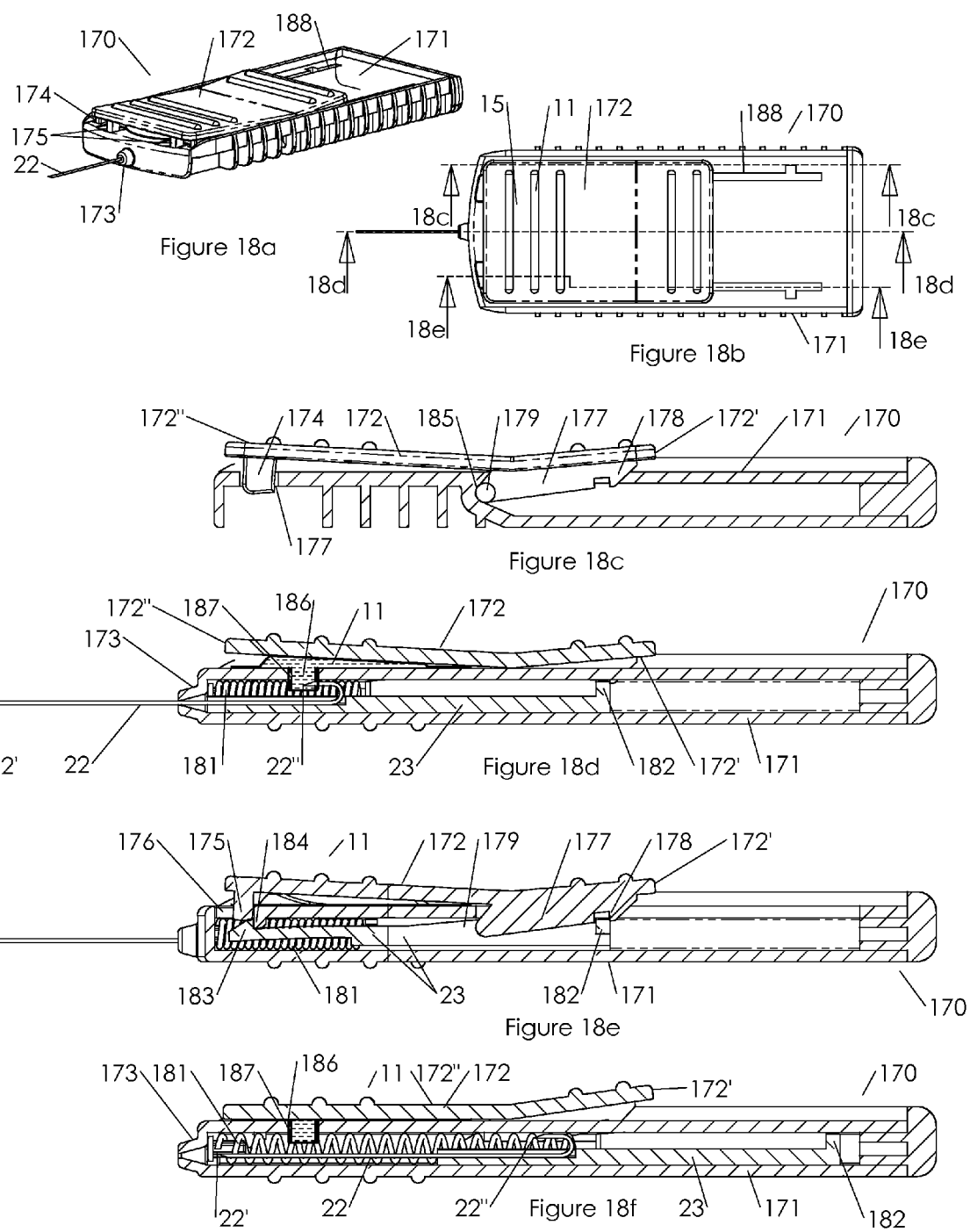

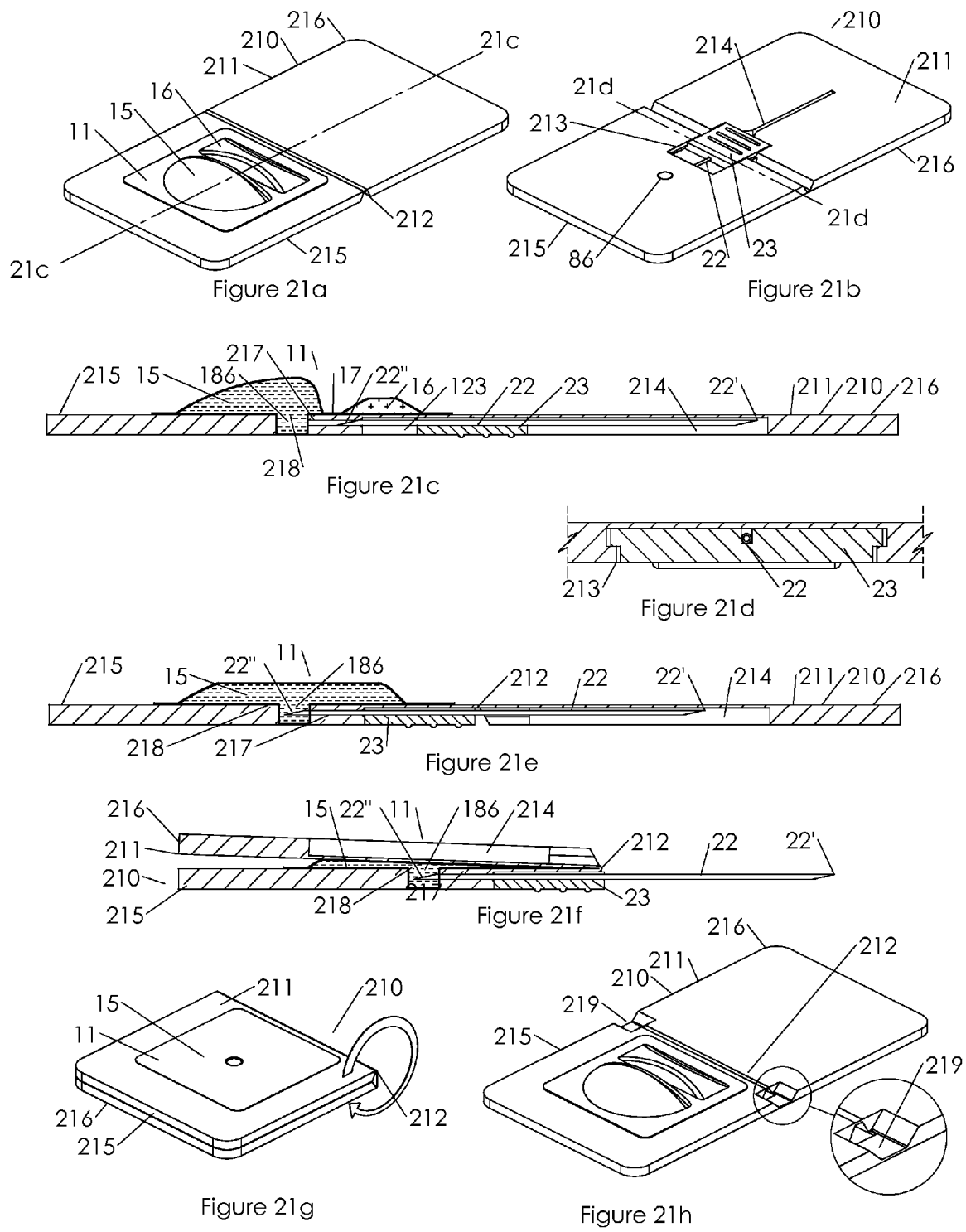

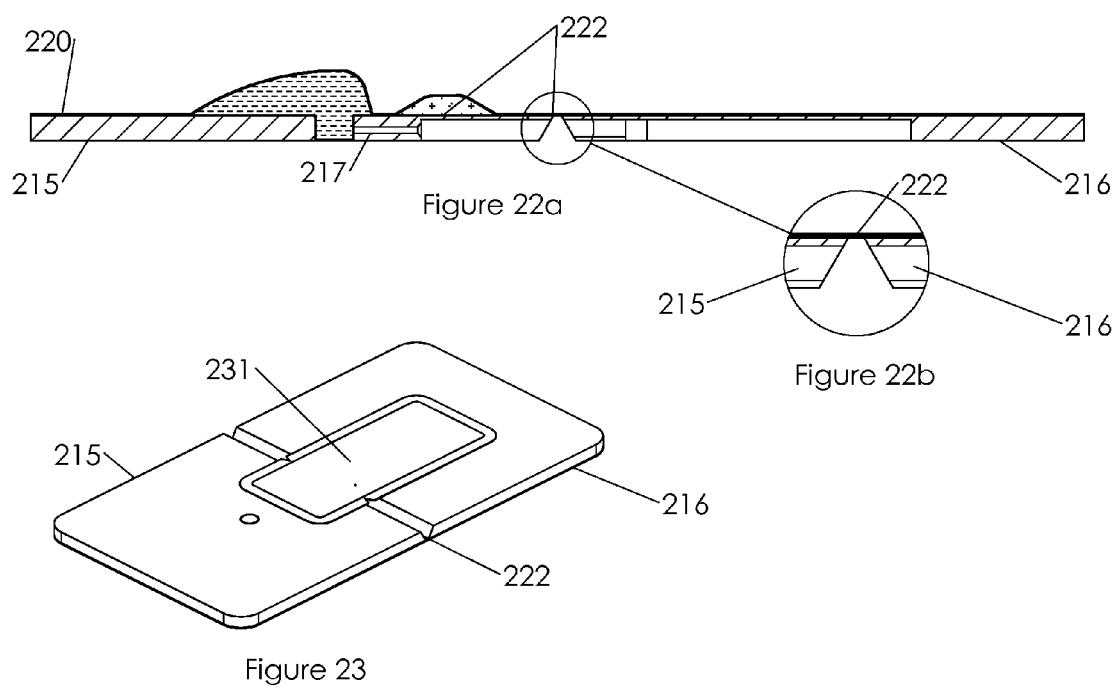
Figure 22a
Figure 22b
Figure 23
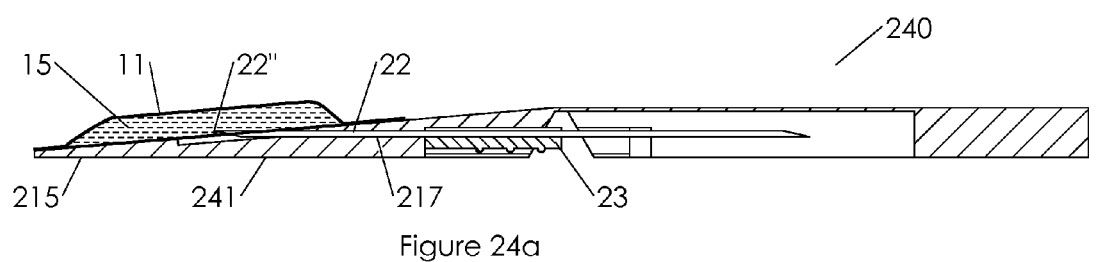
Figure 24a
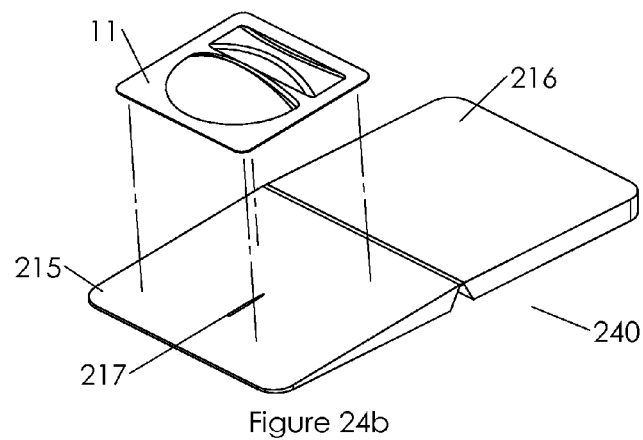
Figure 24b

DISPENSER AND THERAPEUTIC PACKAGE SUITABLE FOR ADMINISTERING A THERAPEUTIC SUBSTANCE TO A SUBJECT, ALONG WITH METHOD RELATING TO SAME

A single-use, unit-dose hypodermic therapeutic delivery device. The device improves upon the packaging conditions of the therapeutic substances, while allowing for efficient and cost effective manufacturing. In particular the device has the advantages of improved packaging, storage, transportation, preparation, reconstitution, and delivery of dry powder vaccines. In addition, the device's construction allows for convenient destruction after use.

FIELD OF THE INVENTION

The present invention, in one sense, relates to a dispensing package of a unit dose of therapeutic substance and administration of the therapeutic substance to a patient. More particularly the present invention refers to pre-filled film packages where the package is pierced to deliver its content(s).

BACKGROUND OF THE INVENTION

Film or foil packages (generally referred here after as "film packages") are abundant in commercial use for hermetically storing content which is sensitive to environmental condition which can cause its perish. Films can be composed to have superior barrier properties to light, air moisture and other elements encountered in and around the package. State of the art film manufacturing methods allow for combination of several monolayers in a multilayer film each providing complementary properties and qualities to the film. For example aluminum Aluminum-Oxide or Teflon laminates provide superior barrier to moisture and oxygen. Polypropylene or Polyester layer provides goof formability of the film, and PE or EVA outer layers provides excellent heat sealing properties. Thus extreme properties can be incorporated in a multi-layer film without giving up on other important properties. Achieving high barrier wall with injection molded parts (hereafter referred to as molded parts) is more challenging and relatively limited than with film walls. Molded parts are usually made from a single uniform material and where a combination of materials or properties is relatively expensive and complicated to manufacture. Also, while films are produced in a continuous process under uniform constant and controlled conditions which reduce the probability of defects in the product, injection molding cycles involve varying conditions which increase risk of defects in particular if the molded parts involve extreme properties such as very small size or very low wall thickness. Thus molded parts provide inferior barrier properties. Defects in molded parts may include cold weld lines (i.e. a seam between one segment of a part to another which is not a homogenous continuation of the material), a crack of a hole, etc. Thus molded parts provide inferior barrier properties for packaging purposes and therefore are not common in this art. Yet several sophisticated packages, which provide extra functionality, combine molded parts in a film package such that the molded part provides part of the wall of the package and therefore a barrier between the content of the pouch and the surroundings. While providing the extra functionality, the molded part is then the Achilles Heel of the hermetic sealing of the content.

U.S. Pat. No. 6,979,316 discloses an auto-injector for rapid delivery of a bolus of injectable medication. In one exemplary the auto-injector comprises a pouch reservoir where a septum is implemented at one end of the pouch for piercing said pouch with a needle. The text describes the septum to be a barrier between content of the pouch and the surrounding. The text does not support the term "septum" any further but it is assumed, based on the common terminology in the art that the inventors refer to a self-sealing compressed rubber component that can be penetrated by a sharp hollow member, such as a needle, to communicate with the content of the pouch. Common rubber materials for this application include silicon. Septums are in common use in filling sites or outlet ports of infusion bags, or other forms of containers for liquid medications.

In U.S. Pat. No. 3,554,256 a container for packaging and feeding intravenous fluids which includes a flexible tubular container member having sealed ends and an outlet connector disposed midway between the ends of the container for interconnecting with an intravenous tube. The ends of the container member are adapted to be attached to a support so that the container member can be folded over and its ends attached to the support, whereby the outlet is disposed at the bottom of the container member. At least one other connector is located near one end of the container member to permit an additive to be added to the contents of the container.

SUMMARY OF THE INVENTION

A variety of embodiments are described which broadly relate to the dispensing of a dose of a substance to a subject. In the description which follows, the term "film" refers to any thin resilient wall of a reservoir, including flexible sheets, laminated sheets or films, monolayer or multilayer, extruded, blow-molded, blown-films or calibrated (rolled) films, metal foils, etc. The term "pouch" refers to any form of reservoir at list partly constructed from films. The terms "pouches", "blisters", and "compartments" generally refer to packages comprising flexible walls commonly made from film, foil, extruded, blown, blow molded, stamped, cold formed, or thermoformed components.

One embodiment of a device comprises a sealed package that includes a collapsible compartment containing the substance. An administration assembly is joined to the package for relative movement there with. The administration assembly may include a delivery device that is movable from a pre-administration position wherein the delivery device is separated from the substance, to a ready position wherein the delivery device is in fluid communication with the substance. At least one compression panel is associated with a sealed package and movable into an engaged position to collapse the compartment and cause the substance to be dispensed through the delivery device.

In certain embodiments a coupler joins the administration assembly to the sealed package, and to this coupler may be a fitting or a portion of a solid body which houses at least a portion of the administration assembly and the sealed package. A gasket seal or the like may be interposed between the administration assembly and the solution. Where the collapsible compartment comprises a multi-layered film wall, the seal may be interposed between these layers. Further, a reinforcement insert may be joined to a wall of the collapsible compartment to provide the backing for the seal as the delivery device is advanced toward the ready position. The delivery device may be operable to puncture a flexible wall to establish fluid communication with the substance.

A particular embodiment provides a single use dispenser for hypothermic administration of a unit dose of a therapeutic fluid to a subject and comprises a hermetically sealed package including a collapsible first compartment containing a first therapeutic substance, with the first compartment comprising a first flexible wall. A rigid backing supports the hermetically sealed package and an administration assembly is associated with the hermetically sealed package. The administration assembly includes an elongate needle having a piercing end and for penetrating the flexible wall of the first compartment, and extends from the piercing and toward a delivery end for administering the therapeutic fluid. A needle actuator advances the needle from a pre-administration position, wherein the piercing end is separated from the flexible wall of the first compartment, toward a ready position to cause the proximal end to breach the integrity of the flexible wall and establish communication between the therapeutic substance and the delivery and. A hub carries the needle and may be frictionally captured within the coupler. In one embodiment, the hub is threadedly attached to the coupler such that rotation of the hub relative to the fitting advances the needle from the pre-administration position toward the ready position.

The single use dispenser may also include a collapsible second compartment containing a second therapeutic substance and having an associated second flexible wall. Here, a frangible seal is disposed between the first and second compartments and the rigid backing is movably attached relative to the compartments between a flattened state and a folded state wherein the backing collapses the second compartment to cause the frangible seal to rapture such that the first and second therapeutic substances are merged. It should be appreciated that the backing which supports the hermetically sealed package may function to collapse one or both of the compartments, or one or more separate compression panels may be employed for this purpose. Further, the compression panel(s) can be configured to protect the needle when it is in the pre-administration position, and may be movable beyond the engaged state to damage, and prevent further use of, the needle.

Also described is a therapeutic package for use in administering a dose of a therapeutic substance to a subject. Such a package broadly comprises first and second sealed compartments having respective first and second walls, with each compartment pre-filled with a respective first and second therapeutic fluid. A frangible seal is disposed between the two compartments. The compartments can be merged by directly pressing with a finger or by a compression panel that is movable between a disengaged state towards an engaged state where the compression panel collapses the second compartment to cause the frangible seal to rapture such that the first and second fluids are merged.

A still further embodiment provides a dispenser comprising a film package including a collapsible compartment containing the therapeutic substance, an administration assembly joined to the film package for relative movement there with, and a coupler joining the administration assembly to the film package. The coupler may be attached to either an interior or exterior wall of the film package.

A method is also provided for preparing to administer a dose of the therapeutic substance to a patient. According to the method an administration device is provided that includes a sealed package and an administration assembly such as described above. The administration assembly is advanced from the pre-administration position toward the ready position causing the proximal piercing and of the delivery device to breach the integrity of the sealed package and establish fluid communication between the therapeutic substance and the distal delivery end. The sealed package may then be compressed with the compression panel to dispense the therapeutic substance through the distal delivery end. The administration assembly may include a protective covering for the delivery device, whereby advancement from the pre-administration position toward the ready position is initiated upon removal of the protective covering. Advantageously also, a portion of the administration assembly may be rotatable to cause the piercing end to puncture the sealed package. A restorative force may then be applied to return the delivery device to the pre-administration position from the ready position.

The present invention further discloses a device comprising a package and an administration assembly. The package and administration assembly can be separately manufactured and then joined at a later manufacturing step or by a user, and thereby reducing manufacturing complexity and providing logistic and operation flexibility.

The present invention further discloses a compartment containing a substance. The compartment is integrally made from film such that the boundaries of the compartments are solely defined by said film, and where a dispensing assembly is manipulated to break the integrity of the package and communicate the substance with the dispensing end of the administration device.

These and other aspects of the present invention will become more readily appreciated and understood from a consideration of the following detailed description of the preferred embodiments when taken together with the accompanying drawings, in which:

BRIEF DESCRIPTION OF THE DRAWINGS

FIG. 1 demonstrates method for fabricating a device according to the present invention;

FIG. 13 demonstrates another preferred embodiment of the present invention which comprises automatic piercing mechanism;

FIG. 17 demonstrates another preferred embodiment of the present invention comprising a self piercing means and needle extraction and retraction mechanism;

FIG. 18 provides more details of the embodiment of FIG. 17;

FIG. 21 demonstrates another preferred embodiment of the present invention where the device has a shape of a credit card with folding hinge;

FIG. 22 demonstrates an embodiment mostly similar to that of FIG. 21 but with a different folding hinge;

FIG. 23 demonstrates an embodiment mostly similar to the embodiment of FIG. 22 but with a different detent mechanism as well as a disinfectant package;

FIG. 24 demonstrates another preferred embodiment of the present invention mostly similar to the embodiment of FIG. 21 but where the piercing happens in a different fashion;

DETAILED DESCRIPTION OF THE INVENTION

Figures 2A, 2B, 2C, 2D:
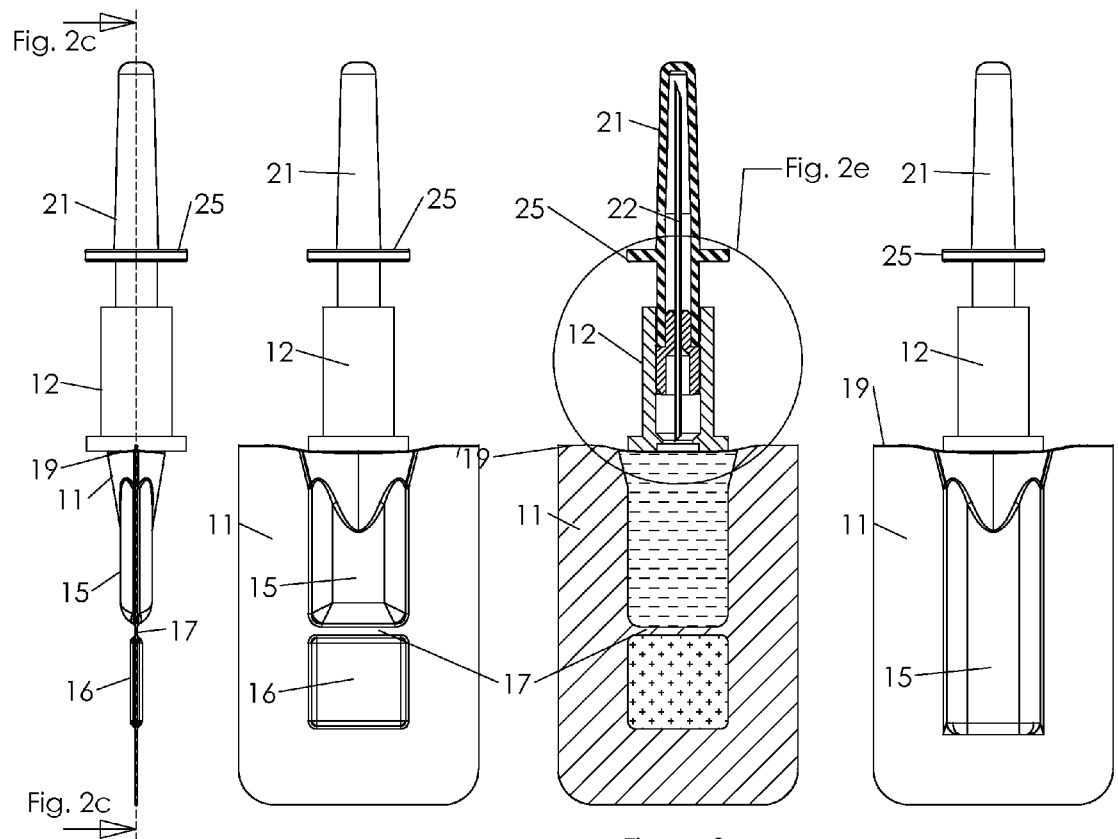
FIG. 2 demonstrates a preferred embodiment of the present invention.

In the following detailed description, reference is made to the accompanying drawings which form a part hereof, and in which is shown by way of illustrations specific embodiments for practicing the invention. The leading digit(s) of the reference numbers in the figures usually correlate to the figure number, with the exception that identical or common components which appear in multiple figures may at times be identified by the same reference numbers. The embodiments illustrated by the figures are described in sufficient detail to enable those skilled in the art to practice the invention, and it is to be understood that other embodiments may be utilized and changes may be made without departing from the spirit and scope of the present invention. The following detailed description is, therefore, not to be taken in a limiting sense, and the scope of the present invention is defined only by the appended claims.

Referring now to FIGS. 1a-1g, the steps of fabricating a preferred package 10 of the present invention is demonstrated. Referring to FIG. 1a, a portion of a thin film cut to shape and size is demonstrated 11. The film 11 can be made of mono layer or multi-layer plastic, metal, metal oxides, glass or a combination thereof. Other film materials known in the art are applicable. FIG. 1b demonstrates the film portion 11 after a fitting 12 has been attached to it on a folding line 19. The fitting 12 is preferably made of plastic material and is attached to the film 11 by one of the means known in the art including heat stake welding, ultrasonic welding, RF welding, hot plate welding, adhesives, or mechanical engagement such as snap feature or pressure fit to a member located of the opposite side of the film 11. FIG. 1c demonstrates a step in the fabrication of the package 10 where two panels of the film 11 are folded along the folding line 19. The film 11 adjusts itself to accommodate the rigid fitting along the folding line 19. FIG. 1d demonstrates a fabrication step of the package 11 where a first compartment 15 is formed by welding a defined area 14 of the film 11 between the two opposite folded sides. The geometry of the welding 14 allows for the film portion 13 around the fitting 12 to naturally blend in with compartment 15. The welding of the film walls 11 can be made by any of the means know in the art including ultrasonic, RF, heat stake, hot plate, etc. Alternatively the walls can be adhered rather than welded. FIG. 1e demonstrates a subsequent step in the fabrication of the package 11 where the first compartment 15 has been filled and sealed and a second compartment 16 has been formed. The sealing portion 17 between the first compartment 15 and the second compartment 16 is frangible such that under the presence of pressure in at least one of the compartments 15 or 16 the attachment of the opposite walls in designated portion 17 will separate (or rupture) allowing said two compartments to merge, while the perimeter sealing of the compartments 15 and 16 remains tightly sealed. The weaker joint of the films at the frangible seal 17 can be achieved in various ways known in the art including use of different sealing conditions (such as welding temperature, welding pressure, or welding time), apply specific sealing geometry, or selective coating or passivation of the sealing layer. FIG. 1f demonstrates a subsequent step of fabricating the package 11 where the second compartment is sealed resulting in a completely hermetically sealed package. Unlike most of the film packages with fitment which are commercially available, where the fitting is inserted between the film walls which construct the compartment and therefore are in direct contact with the content of the package, the content of compartments 15 and 16 are solely exposed to the film 11 inner layer providing a superior barrier from environmental conditions. FIG. 1g demonstrates a subsequent stage of the fabrication of the device 10 where a dispensing assembly 18 is attached to the fitting 12.

The dispensing assembly, also referred to in this embodiment and others as an administration assembly, moves relative to the sealed package and communicates the content of the package to the target to which the content is ultimately applied. A coupler, such as a fitting or fitment, joins the administration assembly to the sealed package. The administration assembly includes a delivery device, and it comprises a proximal end including at least one mean for communicating the content of the package to the dispensing assembly in a sealed fashion; and a distal end comprising at least one applicator for the particular application of the device. In some embodiments the applicator is a canula or a needle for invasive administration of the contents of the package to a tissue of a subject such as intradermal injection, subcutaneous injection, intramuscular injection or other injection methods known in the art for medical, cosmetic, veterinary, or other commercial dispensing applications. In other embodiments the applicator is a dropper tip or a spray head for topical applications, oral applications, enteral applications, parenteral applications, opthalmological applications, nasal, or ear treatment or other medical, veterinarian, cosmetic, beauty or commercial applications known in the art. In yet other embodiments the applicator is a surface applicator such as a brush, pad, sponge for one of the applications described above. In yet other embodiments the dispensing assembly comprises a connector or a fitting to connect to any of the above applicators or to connect to a tube or a bag to which the content of the package is to be dispensed. Commercial applications include dispensing of glue, paint or dyes or samples of such, chemical agents for diagnostic or titration, glues, or other commercial applications known in the art. It will be obvious to those skilled in the art that dispensing assembly may include plurality of applicators or a replaceable applicator.

Figures 2E, 2F, 2G:
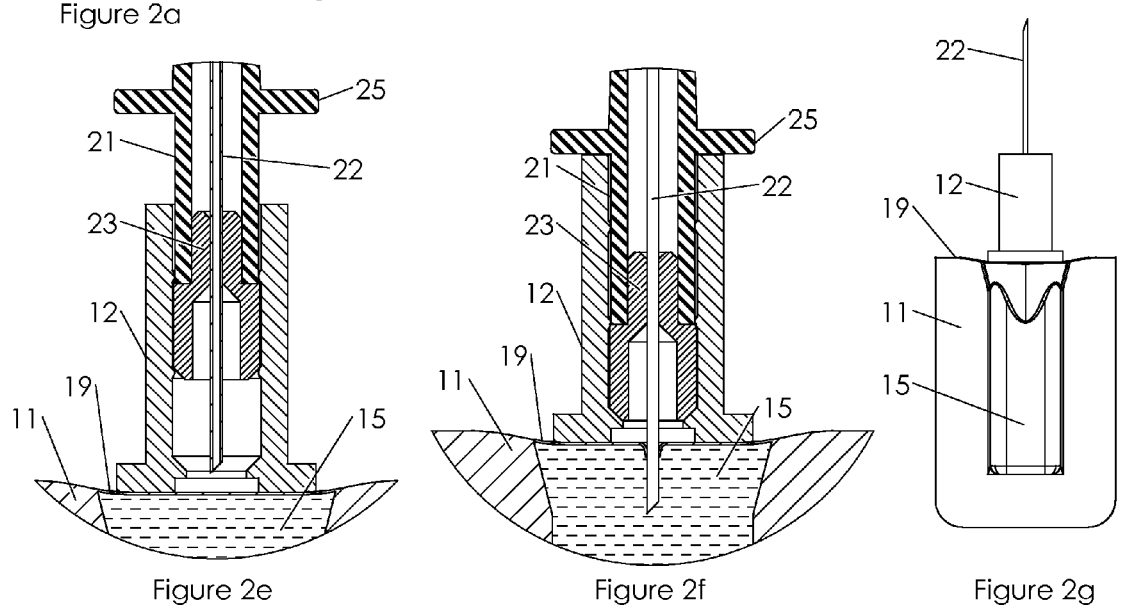

Referring now to FIGS. 2a-2g, a preferred embodiment of the present invention is demonstrated. FIGS. 2a and 2b show general views at the pre-administration (or rest) position, i.e. the position in which the device is during storage, transportation and until it is used. The pouch 11 has the fashion as demonstrated in FIG. 1, and an elongated fitting 12, broadly a coupler, is attached to the pouch along the folded section of the pouch 19. A needle protector 21 is accommodated at the distal end of the fitment 12. The first compartment 15 is separated from the second compartment 16 by a frangible seal 17. FIG. 2c demonstrates a section view along the section line in FIG. 2a, revealing a needle 22 having a distal sharp end to facilitate penetration of the needle to the body of a subject, and a proximal end for piercing the pouch 11 in order to establish fluid communication between the needle 22 and the fluid in the reservoir 15. FIG. 2d demonstrates the device after the first and the second compartment were merged and its contents mixed such that the fluid in the reservoir 15 is now ready for administration. FIG. 2e demonstrates an enlarged detail view of a portion of FIG. 2c. The needle 22 passes through a needle hub 23 which is frictionally held within the fitting 12. It is to be noted that needle 22 has a sharpened inner end portion 20 for penetrating the of pouch 11 and a sharpened outer end portion for use in administering the drug or vaccine to a subject.

A needle protector 21 having a diameter such that it can fit within fitting 12 is, for storage and shipment, lodged with its open end fitting within the open end of fitting 12 and held in position by a combination of friction and an inwardly projecting annular ridge which abuts hub 23. Needle protector 21 functions as an actuator for advancing the needle from the pre-administration position toward the ready position. Protector includes an outwardly projecting flange 25 to control the movement when preparing to administer the solution by forcing needle to breach the integrity of the pouch's 11 wall.

Referring now to FIG. 2f, the device is shown in the ready position after the needle protector 21 was pushed toward the fitting 12 thereby manipulating the proximal sharp point of needle 22 to penetrate the pouch wall 19. The pierced portion of the wall 19 establishes a fluid tight seal against the needle 22 thus ensuring that the medication flows strictly from the reservoir 15 to the distal end of the needle 22. Referring now to FIG. 2g, following the piercing of the wall 19 the needle protector 21 is removed and can be retained for use as a protective cover over the needle 22 once the injection has been administered.

Figure 3A:
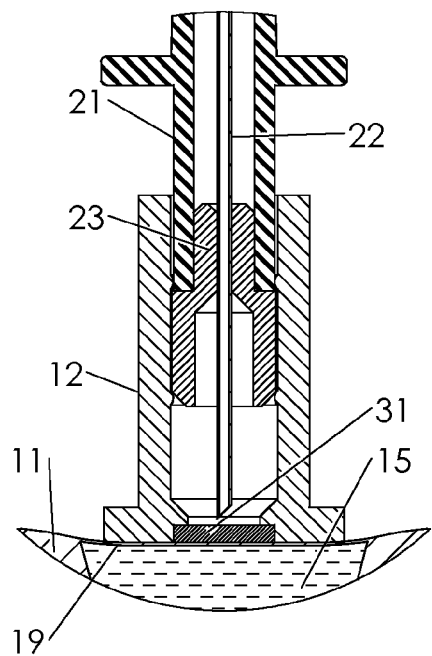
FIG. 3 demonstrates a preferred means for sealing between the needle and the reservoir including a rubber gasket.
Figure 3B:
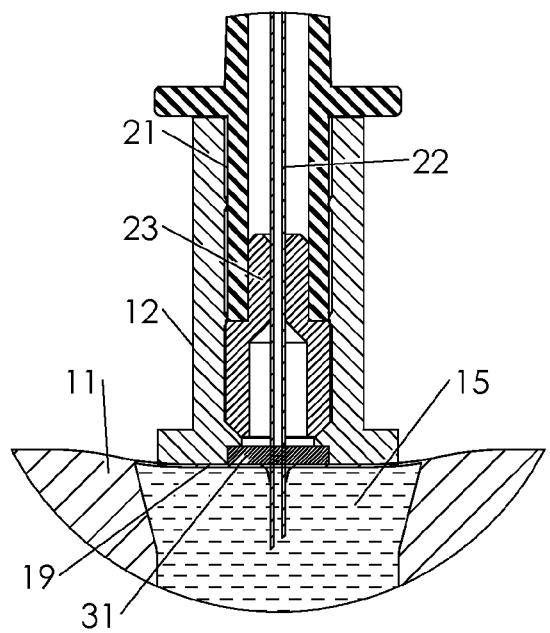

Referring now to FIGS. 3a & 3b a further preferred embodiment of the present invention is demonstrated which is mostly similar to the configuration of FIG. 2 except for the addition of a sealing member in a form of a gasket 31 disposed between the fitting 12 and the pouch's wall 19 to facilitate the sealing of the needle 22 to the reservoir wall 19. The gasket 31 is made from a resilient material compatible with the specific application and the manufacturing processes, and in most applications latex or silicone rubbers are adequate. In one embodiment the gasket 31 is compressed either radially or axially or both to increase the compression of the gasket 31 on the needle 22 when the last penetrates thereby improving the sealing. The gasket 31 can be held in position by merely being confined between the pouch wall 19 and the fitting 12, or alternatively can be attached to either the fitting 12 or the pouch wall 19 by one of the means known in the art. FIG. 3a demonstrates a detail of a section view exposing the piercing arrangement in the rest position. FIG. 3b demonstrates the device after the piercing mechanism has been activated: the needle protector is advanced toward the pouch 11 causing the needle hub to displace toward the hub and the needle 22 to penetrate the gasket 31 and the pouch wall 19.

Figure 4A:
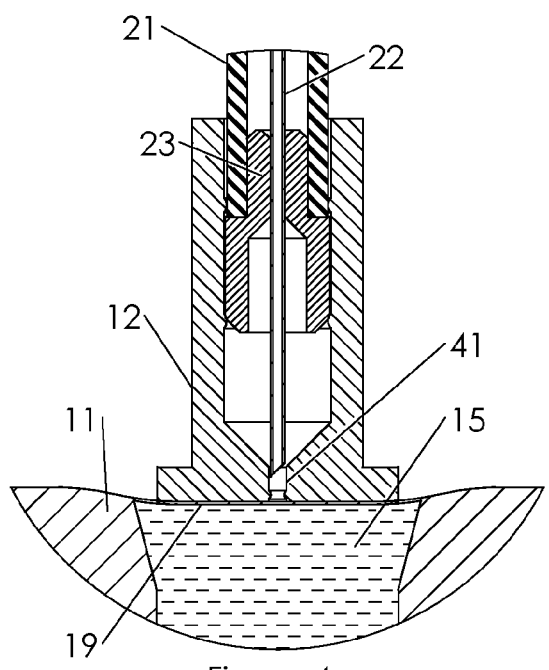
FIG. 4 demonstrates a preferred means for sealing between the needle and the reservoir using radial sealing to the needle.
Figure 4B:
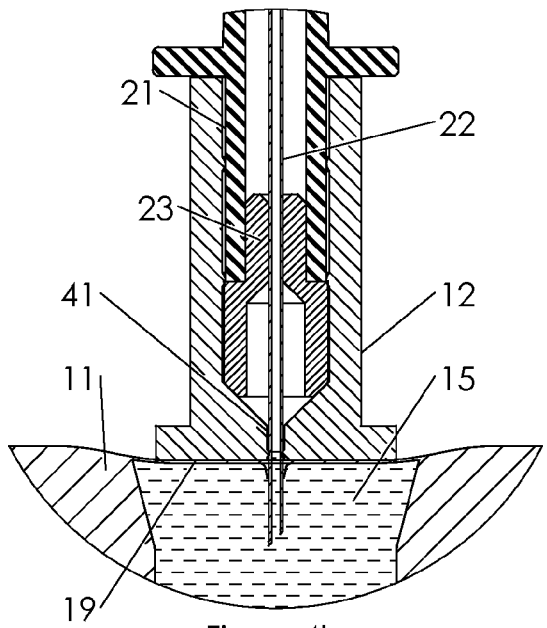

Referring now to FIGS. 4a & 4b, another preferred embodiment of the present invention is demonstrated, which is mostly similar to the configuration of FIG. 2 with the exception that a different sealing mechanism between the needle 22 and the reservoir 15 is implemented. Here, the fitting 12 comprise a narrow section 41 that press fits against the needle 22 in a fluid tight seal fashion. The piercing mechanism is similar to that of the configuration of FIG. 2. FIG. 4a demonstrates the rest position, and FIG. 4b demonstrates the pierced position.

Figure 5:
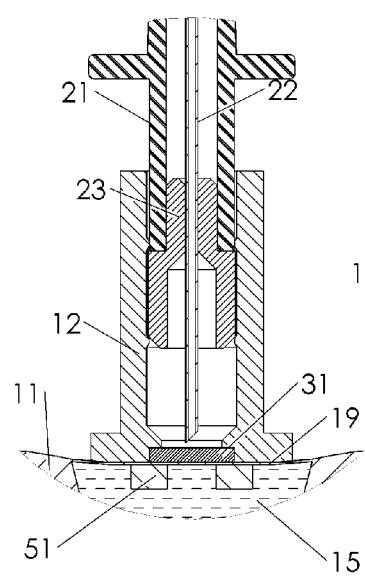
FIG. 5 demonstrates a preferred means for sealing between the needle and the reservoir comprising a support insert in the reservoir.

Referring now to FIG. 5, a further preferred embodiment of the present invention is demonstrated in which an annular reinforcement insert 51 supports the inside of the pouch wall 19, thereby to: a) reduce the tendency of the wall 19 to stretch downwardly during piercing, b) provide a rigid backing for compressing the gasket 31 against fitting 12, c) provide a protection to the sharp piercing end of the needle from getting in contact with the pouch walls 11. The insert 51 can be made from thermoplastic material such as polypropylene or polyethylene and is attached to the inside of the wall 19 by one of the suitable means known in the art such as heat welding or gluing.

Figure 6:
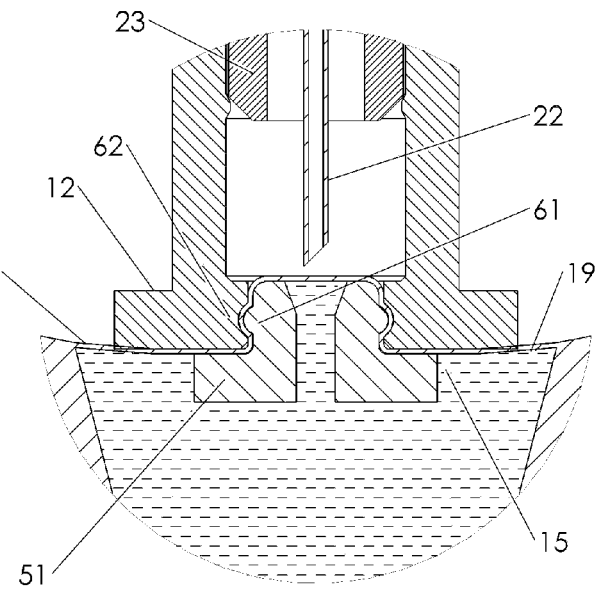
FIG. 6 demonstrates a preferred means for attaching the fitment to the pouch using an insert with a snap fit.

FIG. 6 demonstrates another preferred embodiment where the insert 51 and the fitting 12 are attached to the wall 19 through a mechanical engagement between the fitting 121 and the insert 51 through the wall 19, potentially avoiding the direct attachment between the fitting and the wall 19 or the insert 51 and the wall 19. A protrusion of the insert 51 comprises a snap feature 61, in the form of a lateral radial ridge, that is forced into a reciprocal recess with a radial lateral groove 62 in the fitment 12.

Figure 7:
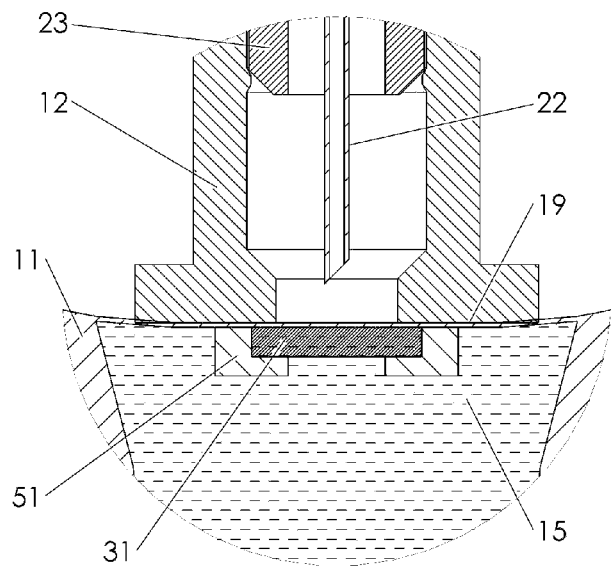
FIG. 7 demonstrates a preferred means for sealing between the needle and the reservoir including an insert with a gasket.

FIG. 7 demonstrates another preferred sealing between the needle 22 and the reservoir 15 where a gasket 31 is accommodated between the insert 51 and the inside of the wall 19.

Figure 8:
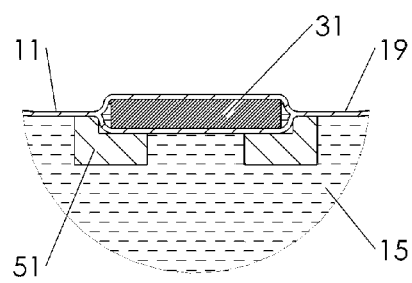
FIG. 8 demonstrates an embodiment of the pouch where a gasket is incorporated in the wall of the pouch.

FIG. 8 demonstrates a further preferred embodiment of the pouch of the present invention where the gasket 31 is implemented between the layers of the film wall 19.

Figure 9A:
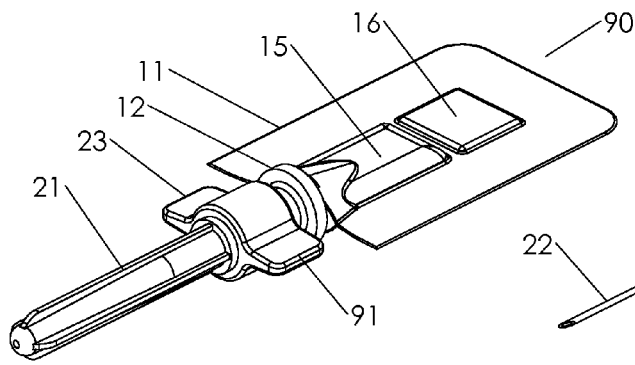
FIG. 9 demonstrates another preferred embodiment of the piercing mechanism where the piercing is activated by quarter turn of the needle hub.
Figure 9B:
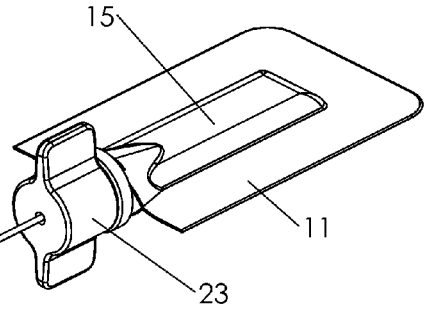
Figure 9C:
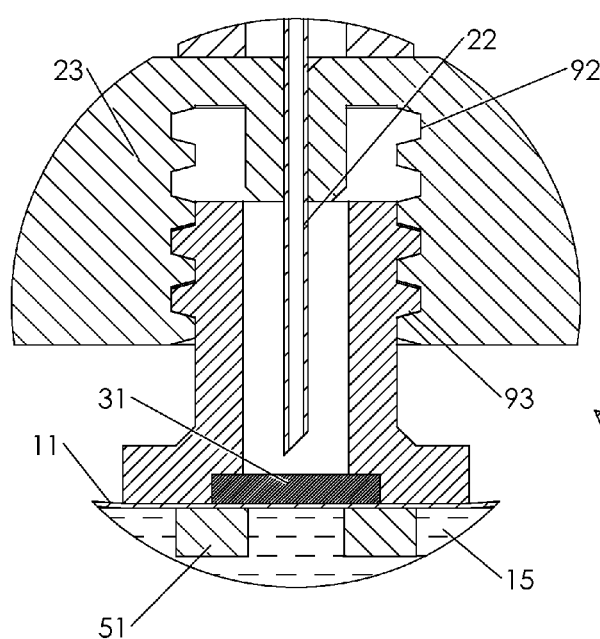
Figure 9D:
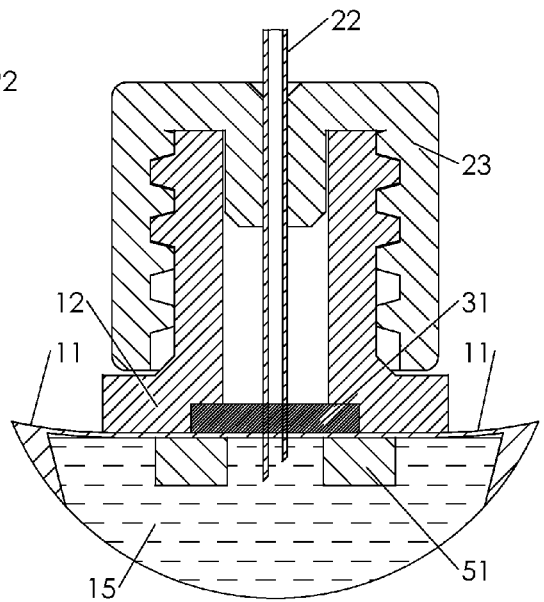

Referring now to FIG. 9a-9d, a further preferred embodiment is demonstrated where the piercing of the pouch 11 is due to a quarter turn of the needle hub 23 rather than pushing inward as it was in previous configurations of FIGS. 2 to 8. FIG. 9a demonstrates the rest position of the device 90. The needle hub comprises lateral protrusions 91 for facilitating the turning action with a finger and thumb. FIG. 9b demonstrates the device 90 when the pouch is pierced and the device is in a ready state for administration. After merging compartment 16 to compartment 15 and mixing their contents, the hub 23 is turned a quarter turn clockwise to pierce the reservoir wall 19, and thereafter the needle protector 21 is removed making the device ready for administration. FIG. 9c demonstrates a detailed section view of the piercing mechanism of the device 90 at the rest position. The hub 23 comprises an internal threaded bore 92, engaged with external threads 93 on the fitting 12. FIG. 9d demonstrates the same view as FIG. 9c after the hub 23 has been turned clockwise, causing the hub 23 to travel axially toward the pouch 11 and the needle 22 to pierce the pouch wall 19.

Figure 10A:
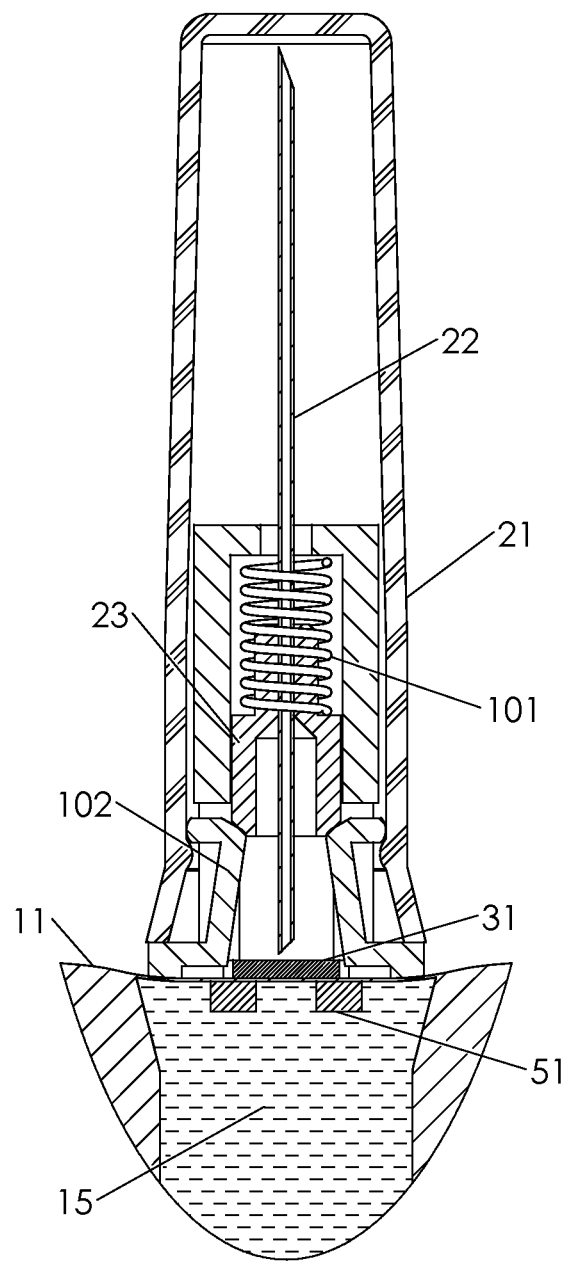
FIG. 10 demonstrates another preferred embodiment of the present invention where automatic piercing is activated by removing the needle protector.
Figure 10B:
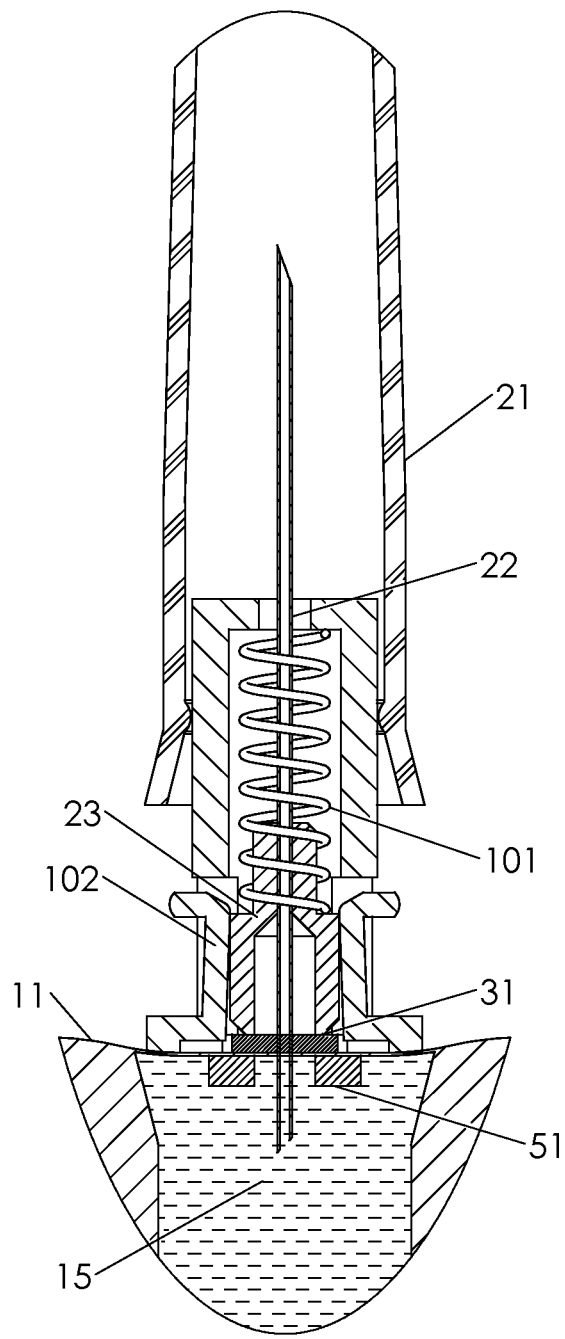

FIGS. 10a & 10b demonstrate another preferred embodiment of the present invention comprising an automatic piercing mechanism which is activated at the removal of the protector 21. Referring to FIG. 10a, a compressed coil spring 101 is accommodated between the distal end of the fitting 12 and the needle hub 23 biasing the needle hub 23 toward the pouch 11, yet the hub is retained in a offset position from the pouch by detent arms 102. Detent arms 102 have the form of cantilever springs and their tapered contact surface with the hub 23 apply an outward radial force on the arms 102 to disengage from the hub 23. The detent arms 102 are counter-forced inward by the protector 21. Referring to FIG. 10b, as the protector 23 is removed the cantilever arms 102 are free to move outward by the force applied by the hub 23, thereby disengaging from the hub 23. The hub 23, under the force of the spring 101 advances toward the pouch 11 causing the needle to pierce the wall 19.

Figure 11A:
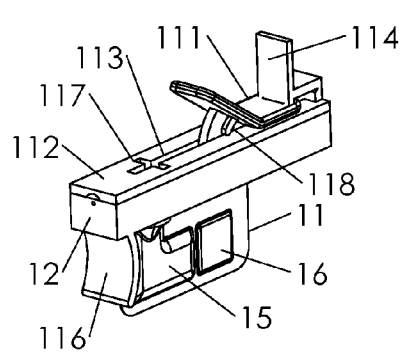
FIG. 11 demonstrates a preferred embodiment of the present invention which comprises safety feature to protect from needle stick injuries.
Figure 11B:
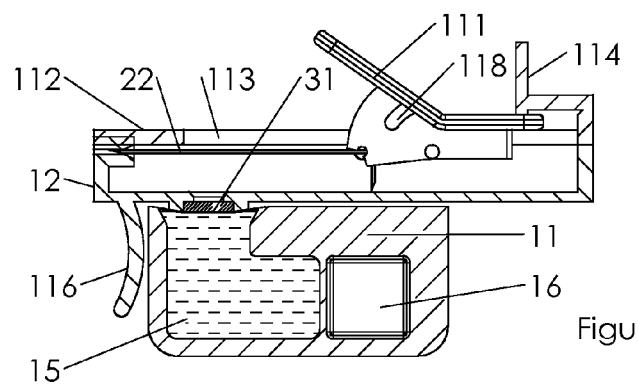

FIGS. 11a-11e demonstrate a further preferred embodiment of the present invention comprising a needle stick safety feature and automatic piercing feature. FIG. 11a demonstrates a perspective view of the device comprising the pouch 11, a fitment 12 having a cover 112 with a mostly longitudinal slot 113 in which a slider knob 111 is disposed and can be operated to travel along said slot to manipulate the needle to the administration extended position, and for piercing the wall of the pouch. Protrusions 118 of the knob 111 lean against surface 112 preventing the knob from rotating when operated, except when the protrusions 118 reach the broadening in the slot 117. In FIG. 11a the device 110 is demonstrated in its rest position in which the needle is confined in the fitting 12. A tamper evident member 114, for indicating whether the device has been previously tampered with, retains the knob 111 in the rest position. Referring now to FIG. 11b a cross-section of the device 110 is shown in the rest position. The fitting 12 comprises a pouch piercing hub 114 and an elongated body in which the needle 22 is disposed, its distal end accommodated in an opening 115 of the fitting 12 and it is attached to the slider 111 next to a bend in the needle 22, while its proximal (piercing end) is free.

Figure 11C:
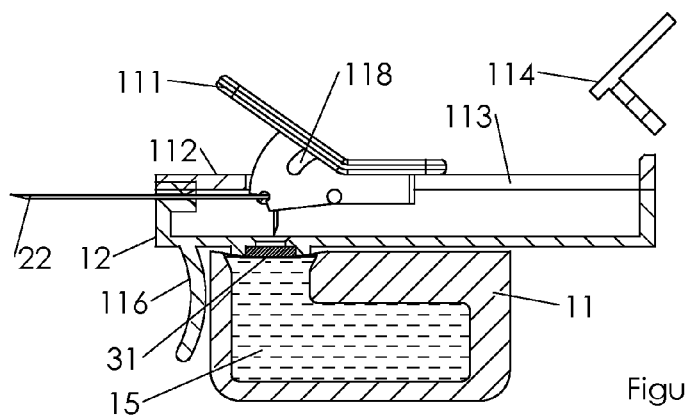
Figure 11D:
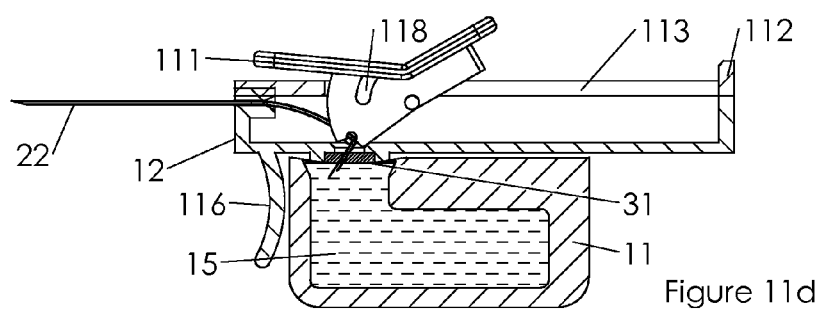

Referring now to FIG. 11c the device 110 is demonstrated at an intermediate instant of the activation action, it being understood at this point that one or more of the compartments, e.g., compartment 16, has been depressed to merge their contents. After compartment 16 was merged with compartment 15, and the fluids in the extended compartment 115 were mixed and ready for administration, the tamper evident piece 114 is broken-off and the knob is operated to advance the needle 22 to extend from the fitting 12. The operation of the knob 111 is achieved by placing the finger on the pad 116, the thumb on slider knob 111 and squeezing the knob 111 forward. In return, the knob 111 slides forward until it hits the end of the slot 113, at which point protrusions 118 are aligned with the broadening zone 117 of the slot 113. Referring now to FIG. 11d, the end position of the knob 111 outward operation is demonstrated in which, under continuation of squeezing the knob forward, the knob 111 tilts counterclockwise thereby causing the needle to bend and the proximal end of the needle to penetrate the piercing hub 114 and pierce the pouch 111. At this position the protrusions 118 are engaged with the broadening zone 117 of the slot 113, holding the knob (and the needle) from moving along the slot 113 during administration. The knob 111 is detained in the rotated position by a pair of detent protrusions (not shown) that engage in the slot 113 at the end of the knob rotation. In a further configuration the force that the needle applies to the knob due to its bending is in a direction which causes a counterclockwise torque to the knob. Such arrangement are some times referred to a self locking mechanism, toggle mechanism, or over-center mechanism. At the end of the administration the knob 111 is manipulated back to the original position thereby disconnecting the needle 22 from the reservoir 15 and hiding the distal end of the needle 22 in the fitting 12.

In a further embodiment a compressed spring is disposed in the fitting 12 along its longitudinal direction such that it biases the knob 111 to the rest position, causing the knob 111 to return to the backward position as soon as the knob 111 has been rotated back from the administration position.

Figure 11E:
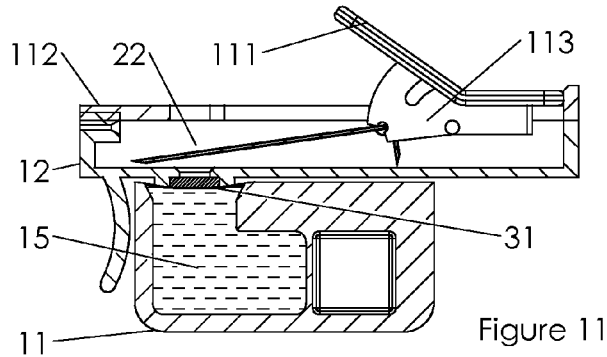

FIG. 11e demonstrates the position of the device after the knob has been retracted to the rear most position. As the tamper evident 114 is now absent, the knob 111 retracts to a further backward position than the rest position. At this position the distal end of the needle 22 disengages from the opening 115 such that any subsequent attempt to operate the knob to the extended position of the needle, is prevented as the needle hits the wall of the fitting 12. In one embodiment a constant tension on the needle 22 ensures that the needle 22 tip will be removed sidewards from the opening 115.

Figures 12A, 12B, 12C, 12D, 12E:
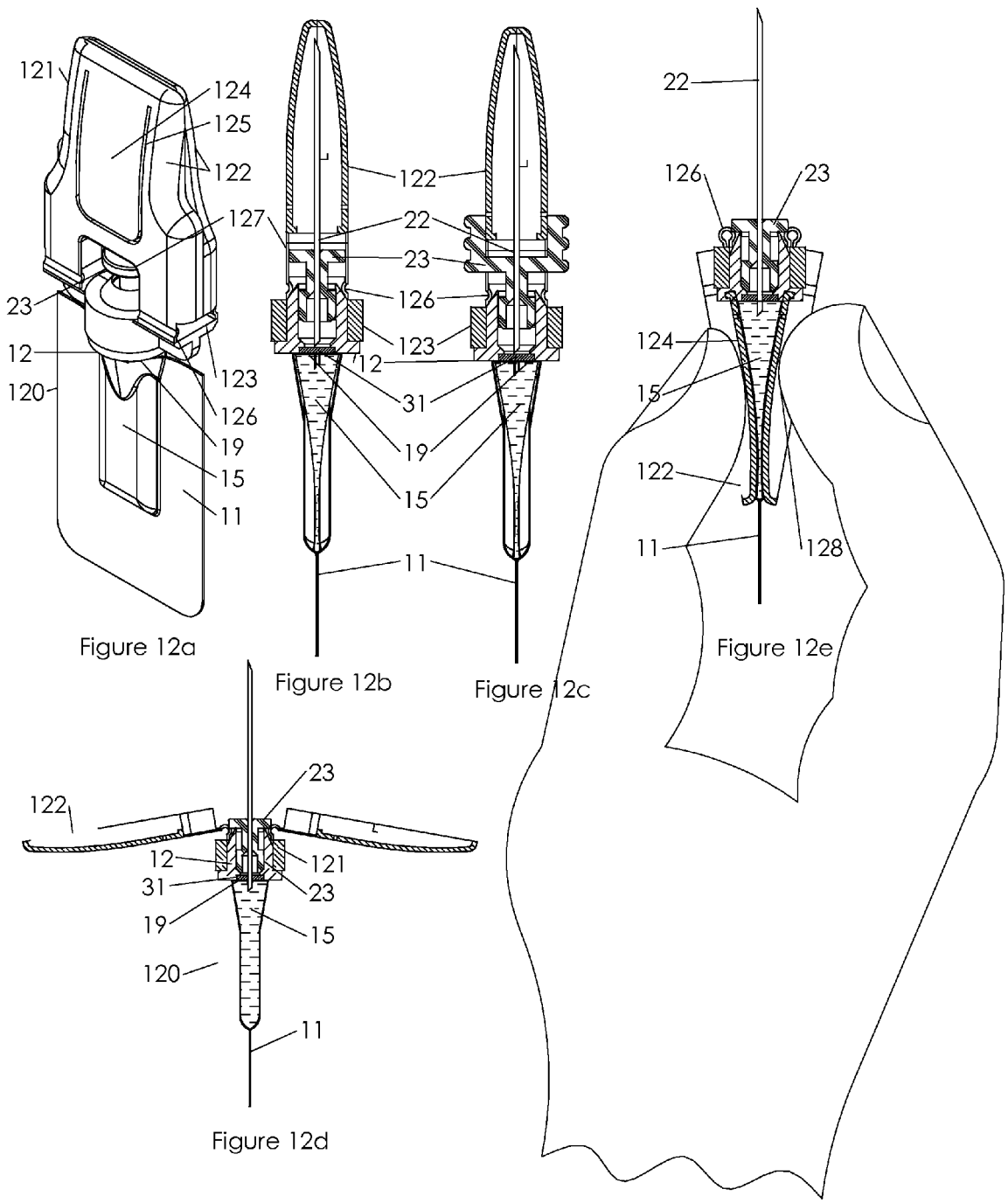
FIG. 12 demonstrates another preferred embodiment of the present invention which comprises means for squeezing the pouch.

Referring now to FIGS. 12a-12e, a further preferred embodiment of the present invention is demonstrated where a device for facilitating the squeezing of the reservoir for administration is provided. FIG. 12a demonstrates a device 120 at the rest position, comprising a pouch 11 which holds a hermetically sealed reservoir 15, and a fitting 12 attached to said pouch 11 confining the pouch's piercing hub (not shown) and a proximal end of a needle 22 for piercing said pouch. The device further comprises a protector having a core 123 firmly connected to the fitting 12 and two rotatable hoods 122, connected to the core 123 by living hinges 126, which cover the distal end of the needle, thus forming a protection from accidental needle stick injuries. In each of the hoods 122 a groove 125 defines a cantilever surface 124 which at a later position will be used as a compression panel for squeezing the reservoir 15 to cause the fluid in said reservoir 15 to expel. FIG. 12b demonstrates a section view of the device 120 at the rest position. The needle 22 is positioned such that the proximal end of the needle is offset from the gasket 31. The needle hub 23 can be reached through opening 127 at the base of the hoods 122 to operate the needle hub 23 to pierce the pouch. Refer now to FIG. 12c which demonstrates a variation on the needle hub 23 which here comprises two vertical arms that prevent the hoods 122 from opening unless the hub 23 has been manipulated down to pierce the pouch, thereby determining the sequence in which the device is to be operated. In FIG. 12d, the device 120 is demonstrated at intermediate instant of opening the hoods 122 in a disengaged state. Where the needle hub 23 has not been operated at an earlier stage to pierce the pouch 11, a clear access to the needle hub 23 allows making the piercing operation at this stage. Referring now to FIG. 12e, a section view demonstrates the device 120 ready for administration. The hoods 122 has been fully opened such that the compression panels 124 are leaning against the reservoir 15 in an engaged state and the internal side of the cantilever surfaces 124 are used as squeezing pads. Squeezing the reservoir 15 with the compression panels allows convenient and efficient means for completely emptying the reservoir 15, especially if the last has a surface larger than the finger pads 128. Upon completing the administration the hoods are returned to the rest position to protect for accidental needle injuries. The current embodiment provides improved needle-sticks safety compared with embodiments where a protector is replaced on the needle after use in the axial direction of the needle. In this embodiment the protector panels are pushed from the sides in a manner that the fingers are not exposed to needle sticks In one embodiment a tamper evident feature, showing whether the device has been previously tampered with, needs to be manipulated in order to open the hoods 122. In another embodiment a tamper evident feature is manipulated by opening the hoods 122. In a further embodiment a tamper evident feature needs to be manipulated in order to operate the hub 23 to pierce the pouch 11. In another embodiment the operation of the hub 23 to pierce the pouch 11 manipulates a tamper evident feature. In yet another embodiment a lock feature permanently locks the hoods together when those are returned to the rest position after administration providing an auto-disable feature preventing reuse of the device.

Referring now to FIGS. 13a-13f, a further preferred embodiment is demonstrated which is mostly similar to the embodiment 120 of FIG. 12, with the exception that an automatic piercing mechanism is incorporated in the needle protector. FIG. 13a, and its enlarged detail view in FIG. 13b, demonstrate the device 130 in the rest position A cylindrical sleeve 131 is accommodated concentric with the needle 22, and spaced apart from needle hub 23. The sleeve 131 is connected to two joint arms 132 at one end of the joint arms. The other end of the joint arms 132 are connected to the hoods 122, and at the rest positioned the arms are folded and confined between the sleeve 131 and the hoods 122. FIG. 13c, and its enlarged detail view in FIG. 13d, demonstrate the device 130 at intermediate instant of opening the hoods 122. The end of the arms 132 that are connected to the hoods 122 are pulled out with the hoods, causing the sleeve 131 to move toward, and get in contact with, the needle hub 23. FIG. 13e, and its enlarged detail view 13f, demonstrate a subsequent instant of opening the hoods 122. The arms 132 continue to pull the sleeve 131 down as the hoods continue to open, and as a consequence the sleeve displaces the hub 23 toward the pouch 11 causing the needle 22 to pierce the wall 19.

Figure 14A:
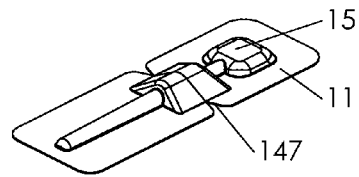
FIG. 14 demonstrates another preferred embodiment of the present invention which comprises automatic piercing mechanism.
Figures 14B, 14C:
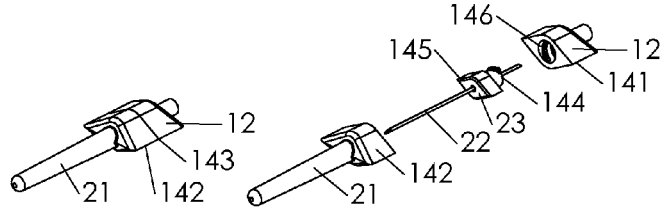
Figure 14D:
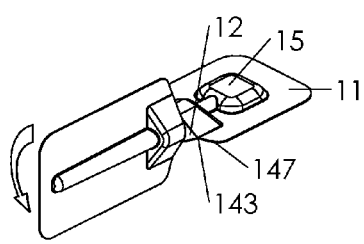
Figure 14E:
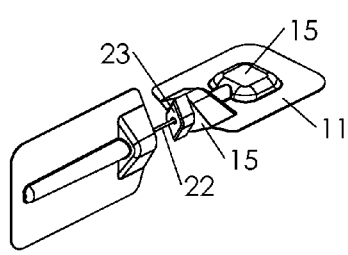

FIGS. 14a-14i demonstrate a further preferred embodiment 140 of the present invention. FIG. 14a demonstrates a general view of the device 140 at a pre-use configuration. The film 11 that constitutes the pouch continues beyond the piercing hub to cover and hermetically seal over the needle protector, such that the entire device is hermetically sealed and the protector can not just be pulled of from the device 140. A slit 147 in the film marks the future point of breaking-off the protector and part of the film from the device 140. FIG. 14b demonstrates the piercing hub 141 and the protector 142, which confine the needle (not shown), prior to introducing to the pouch 11. The piercing hub 141 and the protector base 142 share a common profile terminating by a sharp edge 143. FIG. 14c demonstrates an exploded view of the assembly of FIG. 14b. The needle 22, and the needle hub 23 are now visible. The needle hub 23 comprises an external thread section 144 that engages with an internal thread section of the piercing hub 141, and a flange section 145 that engages with the needle protector 142 when the last in mounted on the needle hub 23. FIG. 14d demonstrates the device 140 when the protector and the section of the pouch film that cover it are turned a quarter turn counterclockwise. Because of the common sharp edge of the protector 142 base and the piercing hub 141, together with the slit 147 in the film in front of the commons sharp edge 143, as soon as the protector starts turning the film is completely sheared separating the needle protector 142 from the rest of the device 140. In FIG. 14e, after the film package has been sheared off by the quarter turn action, the protector can now be removed.

Figure 14F:
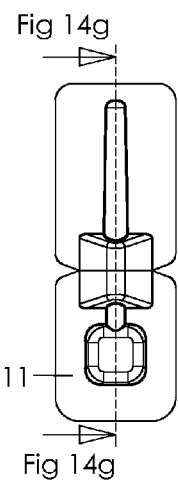
Figure 14G:
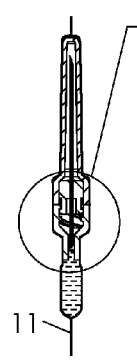
Figures 14H, 14I:
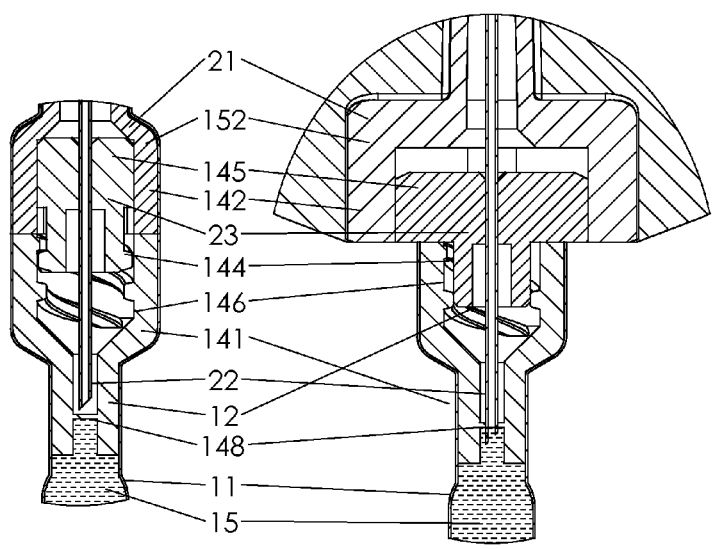

FIG. 14f demonstrates the device in the rest position again providing orientation for the following section views. FIG. 14g orients for the detail view of FIG. 14h. The thread section 144 of the needle hub 23 is engaged with the internal thread 146 of the fitting 141 such that when the needle hub is rotated in a counterclockwise direction the needle hub 23 will advance toward the pouch 11. The flange section 145 of the needle hub 23 is engaged with needle protector base 152 such that turning the protector around the needle 22 axis will turn the needle hub along with it, while the needle hub 22 is free to move outward from the protector base 152 along the needle 22 axis. Thus as the protector 21 is turned a quarter turn counterclockwise to shear the film package the needle 22 will advance toward the pouch 11. FIG. 14h further shows a thin membrane that seals the reservoir 15. FIG. 14i shows a section view of the same configuration as in FIG. 14d, after the protector 21 has been turned a quarter turn in a counterclockwise direction from the rest position. The turn of the protector 21 caused the needle hub 23 to turn and advance out of the protector base 152 and toward the pouch 11 causing the proximal needle end to pierce the membrane 148.

Figure 15A:
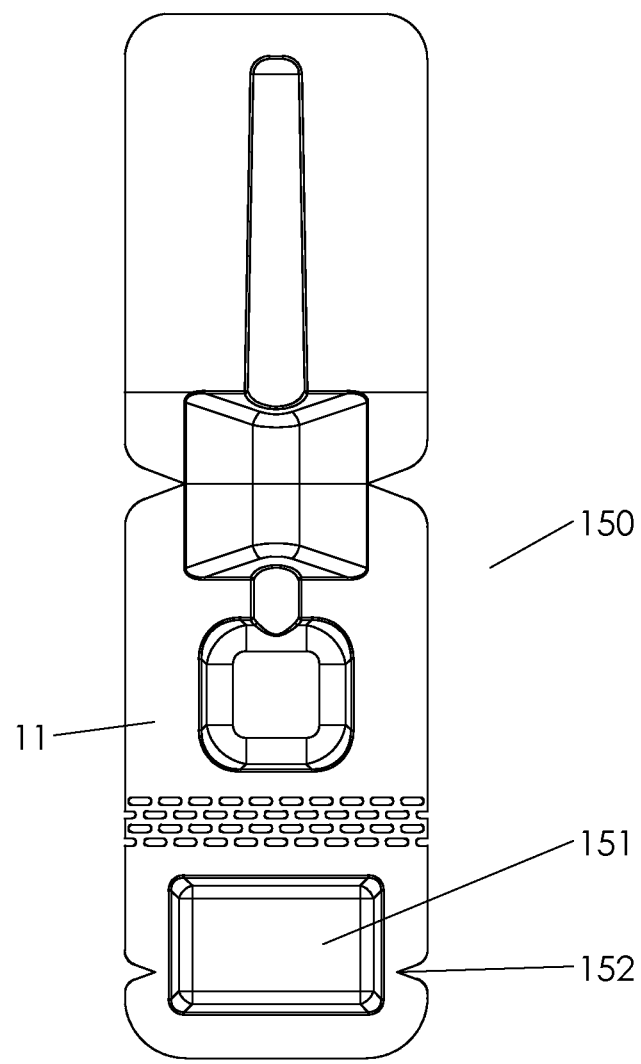
FIG. 15 demonstrates another preferred embodiment of the present invention where the pouch comprises a compartment for topical disinfectant product.
Figure 15B:
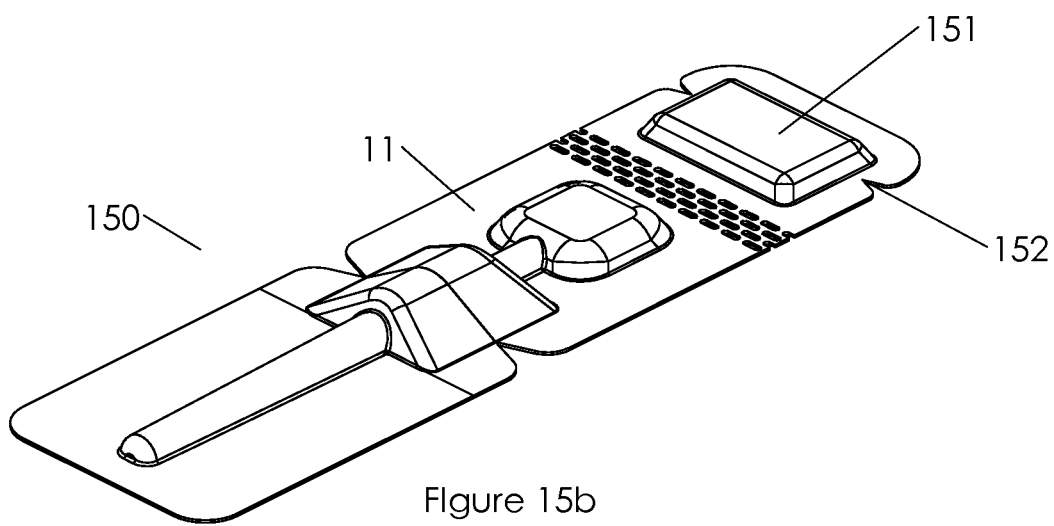

FIGS. 15a-15b demonstrate a further preferred configuration of the present invention which comprises a compartment for disinfectant substance for disinfecting the skin area at the injection site. The pouch comprises a dedicated slit 152 for concentrating the shear forces when opening the disinfectant compartment 151. The disinfectant compartment 151 may contain a liquid, a gel, or other forms of disinfectant ingredients. The pouch may further contain a gauze, a sponge, or any other absorbing matrix known in the art that can contain the disinfectant fluid and facilitate the application to the skin at the injection site. In a further embodiment the arrangement is such that the essential steps for preparing the device for administration are conditioned by or are interfered by first utilizing or at least removing or opening the disinfectant compartment 151.

Figure 16A:
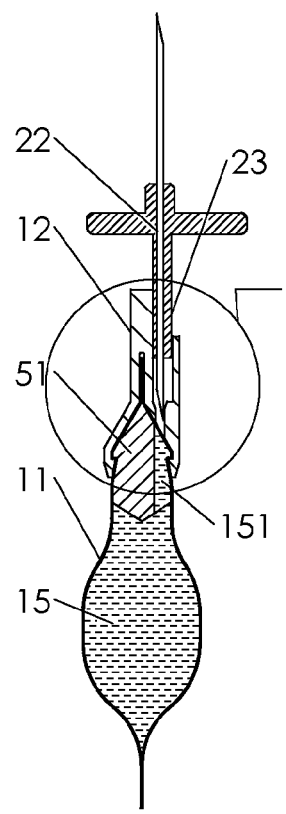
FIG. 16 demonstrates another preferred means for attaching the fitment to the pouch.
Figure 16B:
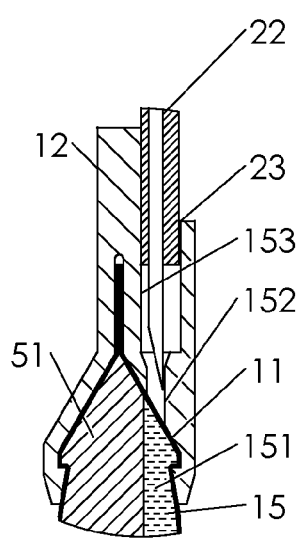
Figure 16C:
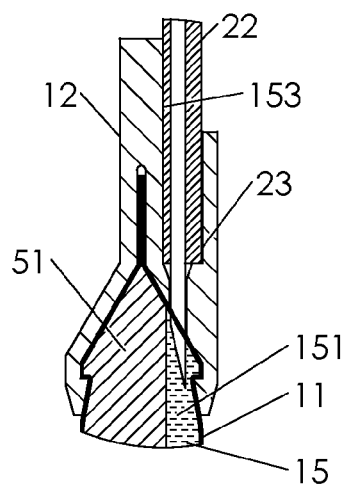

FIGS. 16a-16i demonstrate a further preferred embodiment where the fitting is accommodated on a welded seam of the pouch. FIG. 16a demonstrates a section view for orientation of the following section views. FIG. 16b demonstrates the rest position. The fitting 12 is mechanically engaged with an insert 51 through the wall of the pouch 11. The needle hub 23 is accommodated in a vertical slot 153 in the fitting 12, such that the needle is offset from the seam line of the pouch 11 and is aligned with a conduit 151 in the insert 51. Referring to FIG. 16c, when the needle hub is advanced in the slot 153 toward the pouch, the needle 22 pierces the wall of the pouch 19.

Referring now to FIGS. 17a-17e, a further preferred embodiment of the present invention is demonstrated. FIG. 17a shows the device 170 in a perspective view. The device 170 comprises a housing 171 and a sliding knob 172 accommodated in sliding grooves (not shown) in the housing 171. The package 11 is accommodated on the top surface of the housing 11 and comprises a first compartment 15 and a second compartment 16, separated by a rupturable seal 17 (not shown). The housing 171 conceals a needle assembly which can be extended through opening 173 when activating the device 170. The sliding knob 172 comprises two sets of two teeth 174 and 175 symmetrically disposed along the front edge of the knob 172. It can be appreciated that in this Figure and in the following FIGS. 18, 19, and 20, the housing acts as the coupler and the sliding knob acts as the actuator.

FIG. 17b demonstrates a top view of the device 170. The view provides three section lines for orientation of the subsequent section views. Two sets of two openings, symmetrically disposed in the top of the housing 176 and 177 are designated to accept teeth 175 and 174 respectively, when the knob is advanced to a forward position where said teeth and said openings align.

FIG. 17c demonstrates a longitudinal section cut of the device 170 at the rest position in proximity to the side wall of the housing 171. Note that in this Figure and the following section views FIGS. 17d and e, the knob 172 is shown in its entirety and not sectioned, to better demonstrate the details of this part and their interaction with the device 170. The knob 172 comprise a first surface 172' in parallel and in contact with the top surface of the housing 171 and an inclined surface 172" (hereafter "compression panel") in the front of the knob on which the teeth 174, 175 are disposed. The ends of teeth 174 are sitting against the upper surface of the housing 174. The knob 172 further comprises two vertical ribs 177, engaged in longitudinal grooves in the top of housing 171, each rib 177 comprises a lateral protruding pivot 179, perpendicular to said rib 177, and a latch 178 provided by a notch in the rib 177. The pivot 179 contacts the inside of the upper wall of the housing 171. Thus, in the rest position, the knob 172 is constrained to longitudinal movement by the engagement of the ribs 171 in the said grooves, while the rotation of the knob 172 around the pivot 179 is prevented by the three vertical contact points of the knob 172 with the top surface of the housing 171. A meniscus 185 in the side wall of the housing 171 defines the forward end position of the pivot 179 when the knob 172 is slid forward, at which position the teeth 174 will align with opening 177 allowing the knob 172 to rotate.

Referring now to FIG. 17d a longitudinal section view along the symmetric line of the device 170 in the rest position is demonstrated. A needle 22, connected to a needle hub 23, are disposed in the housing 171 such that they can be moved along the longitudinal direction of the housing 171. The needle 22 is accommodated in a slit in the needle hub 23 and is connected by one of the means known in the art such as press fit or glue. A spring 181 is disposed between the housing 171 and the needle hub 23, biasing the last to the backside of the housing 171. The needle 22 comprises a sharp distal end 22' for penetrating a tissue of a subject, accommodated in an opening portion of the housing 173, and a sharp proximal end 22" at the end of a hooked section of the needle 22 for piercing the compartment 15. The package 11 comprises a first compartment 15 and a second compartment 16 defined between two opposite film walls, and separated by a rupturable welded portion between said walls, and is attached to the front section of the upper wall of the housing 171. The package 11 is attached to the housing 171 by one of the means known in the art including, welding, gluing, mechanical fit, adhesive layer of the film, etc. The first compartment 15 comprises a well 186 extending through an opening in the upper wall of the housing 171 to the inner side of the housing 171. A co annular cylinder member 187 is disposed in the well to improve the sealing against the needle 22 when it pierces the wall of the compartment 15. The hub 23 comprises a detent tooth 182 which is engaged with the latch 178 of the knob 172, such that when the knob 172 is moved along the housing 171 the needle hub 23 and the needle 22 will be traveling along with it.

Referring to FIG. 17e, a combined section view of the device 170 is demonstrated. The needle hub 23 further comprises a snap arm 183 aligned, and in an offset position from opening 176, which comprises an inward protrusion 184 for latching snap arm 183 when the needle hub 23 travels to its forward position.

FIGS. 18a-18e demonstrate embodiment 170 of FIG. 17 in the ready position. After the compartments 15 and 16 were merged and mixed by pressing and mashing the wall of the package 11 with a finger, the knob 172 is forced by pushing forward the compression panel 172" with a finger to the forward position. FIG. 18a provides a general view of the device 170 with the needle 22 now extending from the housing 171 through opening 173. Normally at this position the needle is inserted to a target tissue of a patient, which is not shown here. FIG. 18b demonstrates a top view of the device 170 providing orientation for the subsequent section views. The grooves 188 in the upper wall of the housing in which the ribs 177 (not shown) of the knob 172 engage, are now visible. A widening portion of the groove 188 allows clearance for the pivots 179 to pass through the wall into the housing 171 during the assembly process.

Referring to FIG. 18c, at the front position of the knob 172, the teeth 174 of the knob 172 aligns with opening 177, such that forcing the second portion of the knob 172" further forward or downward will cause the knob to rotate counterclockwise.

Referring now to FIG. 18d, the proximal end of the needle 22" pierced the wall of compartment 15 establishing fluid communication between the fluid in said compartment and the distal end of the needle 22'. The sealing member 187 provides for an improved sealing between the needle and the compartment's 15 wall. The sealing member can be made from rubber materials such as silicone or polyurethane rubber, or a soft plastic material such as PE, a PE/EVA compound, etc. It will be obvious to those skilled in the art that the fluid tight sealing of the needle 22 to the wall 11 can be accomplished by other means. In one embodiments the composition of the actual wall of the package 11 is such that it provides good sealing. Such wall will preferably have a layer of soft thermoplastic such as PE, EVA, Surlin (Dupont) etc. In other embodiment the sealing member is accommodated externally to the package 11 wall. In other embodiments the sealing member is provided by an inward extension of the upper wall of the housing 171. Referring back to FIG. 18d, by continuing to force the compression panel 172" forward (or downward), compartment 15 is depressed by causing the content of compartment 15 to expel through the needle 22 (i.e. the "administration" of the fluid), until the compartment is completely squeezed.

Referring now to FIG. 18e, as the knob 172 reaches the front most position, the snap arms 183 latch with the protrusion 184 of the opening 176 in the upper wall of the housing 171. Due to its rocker construction, as the knob 172 is rotated to squeeze the compartment 15, the latch 178 of the knob is removed from detent tooth 182, thereby disengaging the knob 172 from the needle hub 172. Thereafter, and for the duration of the administration, the needle hub 23 is held in the front position due to the engagement of snap arm 183 and protrusion 184, preventing the spring from pushing the needle hub 23 back in. During the rotation of the knob 172, teeth 175 penetrate through openings 176 and contact snap arm 183 pushing them down toward disengagement of protrusions 184, such that as soon as the administration is completed, the snap arms 183 disengage from protrusions 184, the hub 23 snaps to the backward most position drawing the needle back into the housing.

FIG. 18f demonstrates the discard position of the device 170. The hub 23 is now retracted to a position where it can not reengage with the knob 172, preventing reuse of the device 170, or abuse of residual substance. In one embodiment the knob can not be rotated back from the counterclockwise end position thereby preventing reach to the package 11, thereby preventing potential exposure or abuse of the substance.

Figure 19A:
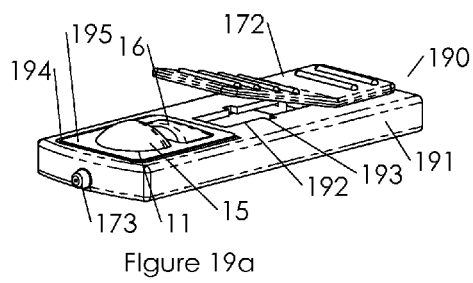
FIG. 19 demonstrates an embodiment mostly similar to the embodiment to FIG. 17 but with a different piecing means.
Figure 19B:
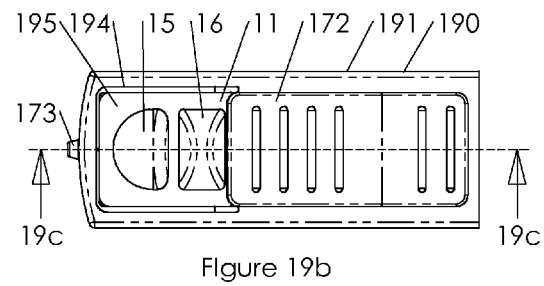

Referring to FIGS. 19a-19e, a further preferred embodiment of the present invention is demonstrated which is mostly similar to embodiment of FIGS. 17 and 18, but for a different method of piercing the package 11. The general operation and function of the knob 172 is similar to that of FIG. 17 and therefore will only be briefly described. FIG. 19a demonstrates a general view of the device 190. A U-shape groove 194 in the upper wall of the housing 191 defines a cantilever portion 195 to which the package 11 is attached. FIG. 19b provides a top view of the device 190 for orientation of the section views in subsequent Figures.

Figure 19C:
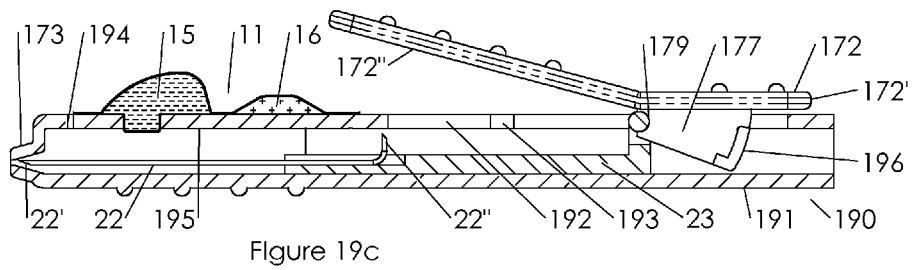

FIG. 19c demonstrates a section of the device 190 in the rest position. The first compartment 15 comprises a well 186 that extends through an opening in the upper wall of the housing 191. The proximal end of the needle 22" terminates with a vertical section.

Figure 19D:
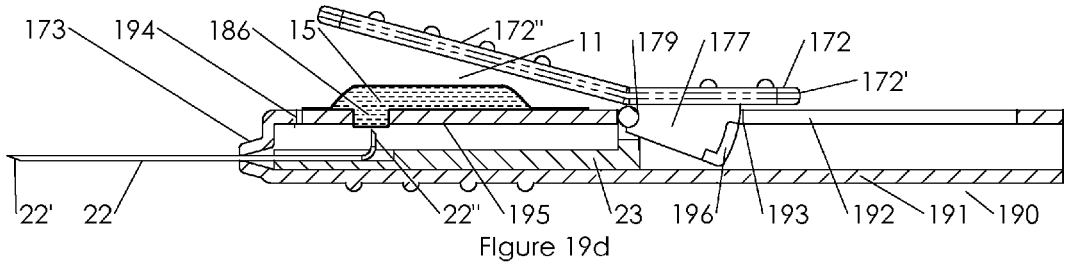
Figure 19E:
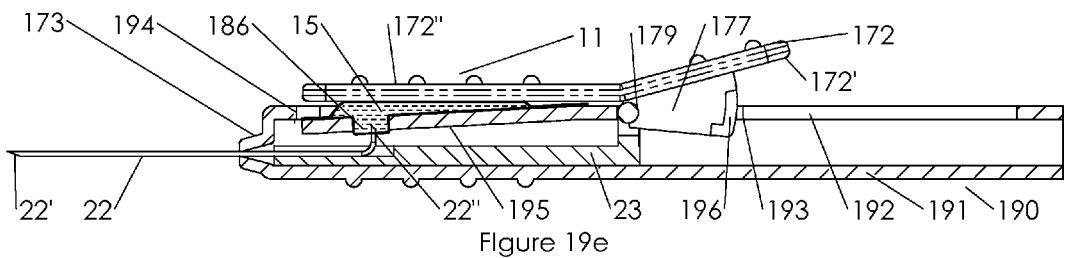

FIG. 19*d* demonstrates the device after the second compartment 16 has been merged to the first compartment 15, and the knob 172 has been moved to the forward position, by pushing on the compression panel 172" forward with a finger. The proximal end of the needle is now aligned with the well 186 of compartment 15.

Referring now to FIG. 19*d*, by further pushing the compression panel 172" forward (or downward), compartment 15 is depressed and as a result causes the cantilever surface 195 to bend down to a point that the proximal end of the needle 22" pierces the wall of compartment 15, establishing fluid communication between the content of compartment 15 and the distal end of the needle 22'.

Figure 20:
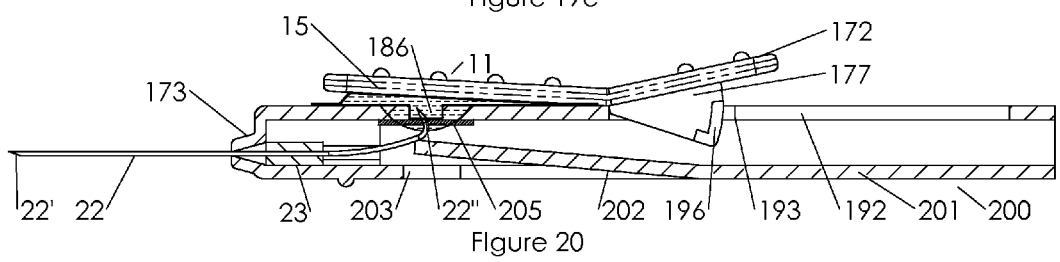
FIG. 20 demonstrates an embodiment mostly similar to the embodiment to FIGS. 17 and 19 but with a different piecing means.

Referring now to FIG. 20 a further preferred embodiment 200 is demonstrated. The device 200 is mostly similar to the device 190 of FIG. 19 but for the different piercing means. The device 200 is demonstrated in the administration position. A u cut in the bottom wall of the housing 201 defines a cantilever section 202. To administer the content of compartment 15 one finger presses the compression panel 172" while another finger provides for an opposite force on the cantilever section 202, such that the cantilever section 202 bends in and forces the proximal end of the needle 22" to bend and pierce the wall of the first compartment 15. A sealing member 205 enhances the sealing of the wall of the well 186 of compartment 15. The sealing member 205 can be made of soft thermoplastic or rubber.

Referring now to FIGS. 21*a*-21*h*, a further preferred embodiment of the present invention is demonstrated. Referring to FIG. 21*a* a perspective view is showing the upper side of the device 210, shown in the rest position. The device 210 comprises a mostly thin and flat body 211 with a general shape of a credit card divided into a first compression panel 215 and a second compression panel 216 (hereafter sometimes referred to as "panel" or "panels"), mostly similar in size to the first panel 215, by a living hinge section 212. The package 11 is attached to the first panel 215. Referring now to FIG. 21*b* a perspective view of the under side of the device 210 is demonstrated in the rest position. A needle 22 and a hub 23 assembly is accommodated in a longitudinal recess 213 that extends between the first panel 215 and the second panel 216, providing clearance for the hub 23 to slide toward the first panel 215. The second panel 216 comprises a slot 214 for accommodating the distal end of the needle (not seen), providing protection to the needle from being damaged prior to use, as well as from sticking injuries from the needle. It can be appreciated, then, from this embodiment that the hub 23 acts as the needle actuator. In fact, in the various embodiments described herein, the actuator can be considered as any pieces which, collectively or separately, function to advance at least a portion of the administration assembly (or particularly, at least a portion of the delivery device) from the pre-administration position towards the ready position. It can also be appreciated that in this Figure and in the following Figures the flat body 211 acts as the coupler.

In one embodiment a label at least partially covers the lower surface of the first and second panels 215,216. In one embodiment the label is at least partially removable. In one embodiment said removable section protects the needle during storage and is removed to expose the needle 22 prior to administration. In one embodiment said removable section of said label prevents access to the needle hub 23, and by removing said peelable section the hub 23 can be manipulated to move toward the first panel 215. In one embodiment said removable section of said label bridges between the first panel 215 and the second panel 216, over the hinge 212 therefore preventing the body 211 from folding, and whereby removing said removable section allows for the body 211 to easily fold. In one embodiment a non-removable section of said label retains the hub 23 in the slot 213.

Referring now to FIG. 21*c*, a longitudinal section view is demonstrated along the symmetry line of the device 210 at the rest position as marked in FIG. 21*a*. The first compartment 15 of the package 11 comprises a well 186 accommodated in a recess in the first compression panel 215. The proximal end of the needle 22" is accommodated in a horizontal bore 217 connecting the slot 213 and the well 186, such that the sharp tip of the proximal end 22" is spaced apart from said well 186. In some configurations the content of the second compartment 16 is powder that needs to be mixed and dissolved with a diluent in the first compartment 115 prior to being administrated. To prevent remaining particles of said powder from reaching the needle 22, the well 186 is capped with a filter 218 such as nonwoven filter attached the wall of the first compartment FIG. 21*d* demonstrates a section view along the line marked in FIG. 21*b*. The hub 23 is engaged with both compression panels 215,216 by an undercut such that the hub is limited to move in the longitudinal direction of the body 211, preventing the panels from folding along the hinge 212.

Referring to FIG. 21*e*, a section view of the device 210 is demonstrated at the initial activation position. Compartment 16 has been merged into compartment 15 by separating the frangible weld line 17. The hub 23 has then been pushed toward the first panel 215 causing the proximal end of the needle 22" to pierce the wall of the well 186 of compartment 15, thereby establishing fluid communication between the content of compartment 15 and the distal end of the needle 22'. The hub is now disengaged from the slot in the second panel 216 allowing the body 211 to be folded i.e. the second panel 216 to be folded over compression panel 215 or vice versa.

Referring now to FIG. 21*f* the administration position is demonstrated where the second panel 216 is folded over the first panel 215 thereby depressing compartment 15 and causing the content of said compartment to expel and to be administered through the needle 22, to a target tissue of a subject (not shown). By folding the second panel 216 the distal end of the needle 22' is exposed and allows for penetration to a tissue.

By small variation in the embodiment of the device 210 the order of the activation steps described above can be switched over. In one embodiment the slot 213 in the second panel 216 does not have the undercut structure as demonstrated in FIG. 21*d* and the second panel 216 folding is not constrained by the hub 23. Therefore the second panel can be first folded over the first panel 215 and only then after the well hub is displaced to pierce the well 186.

Referring to FIG. 21*g*, the discarding position of the device 210 is demonstrated. After completing the administration, the second compression panel 216 is rotated back 180 degrees around the hinge 212 to the opposite folded position of FIG. 21*f*, and by doing so folding and destroying the needle 22. In one embodiment a mechanical latch retains the device in this position, thus providing an auto-disable mechanism for preventing reuse of the device, as well as preventing possible accidental needle sticks after use.

FIG. 21*h* demonstrates an enhancement which furnishes the hinge 212 with a toggle like action in a fashion commonly implemented in cosmetic or other flip-top liquid-container closures. Elastic straps 219 are bridging between the first panel 215 and the second panel 216 of the body 211, in an offset position to the folding axis of hinge 212, such that the straps 219 are stretched in all the intermediate rotational positions between the end positions, and therefore biasing the second flap to one of the end positions demonstrated in the preceding figures. The toggle action may simplify the user's action of folding the second panel 216.

In a further embodiment the device 210 comprises a mechanism for causing automatic piercing of the reservoir when the compression panel is folded over similar to the mechanism disclosed in FIG. 13.

In one embodiment a rubber septum in a form of a sleeve is inserted into the section of the pouch that accepts the proximal end of the needle, to improve the sealing between the needle and the reservoir.

Referring to FIGS. 22a & 22b a further preferred embodiment is demonstrated mostly similar to the embodiment of FIG. 21, but for the hinge connecting between the first panel 215 and the second panel 216. Panels 215 and 216 are now fabricated as separated bodies, and are connected through a film layer that extends over a gap between the two panels, forming a live hinge 222. In one embodiment said film is an extension of one of the walls of package 11.

Referring to FIG. 23 a similar device to devices 210 and 220 of FIGS. 21 and 22 respectively is demonstrated. A pouch 231 comprises an adhesive back is attached to the lower side of panels 215 and 216 preventing the body from folding. In one embodiment the pouch contains a disinfectant substance that needs to be applied to the area where the needle is to stick. The disinfectant substance can be in a form of liquid, gel, paste, loose in the pouch or absorbed in an absorbent matrix such as gauze. By removing the disinfectant pouch the hub can be operated and the second panel can be folded, thereby establishing a critical constrain between using the disinfectant substance and administration the device to a subject.

FIGS. 24a & 24b demonstrate a further preferred embodiment of the present invention in which the first compartment 15 does not comprise a well and therefore is simpler to manufacture and assemble to the device 240. The package 11 is attached to an inclined surface relative to the needle 22 and the needle bore 217 such that the needle penetrates the package in an angle. It will be obvious to those skilled in the art that rather than positioning the package on an inclined surface the proximal end of the needle 22" can be guided in a shoot in the first panel 215, such that during the displacement of the hub 23, it will bend from a direction parallel to the wall of the package to an angle in which it will penetrate the package. FIG. 24b demonstrates how the finished package is assembled to the device assembly. The attachment of the package 11 in simple manner to the external wall of the mechanical device as is true for embodiment 17 to 24 provides an advantageous means of manufacturing as the package 11 can thus fit pharmaceutical packaging machinery, and be manufactured faster and less expensively. The mechanical device on the other hand can be manufactured in a separate line or a separate facility. The package and the mechanical device can be then integrated in a third facility, or just prior to use, providing better manufacturing, storage, and logistic flexibility.

Figures 25A, 25B, 25C, 25D:
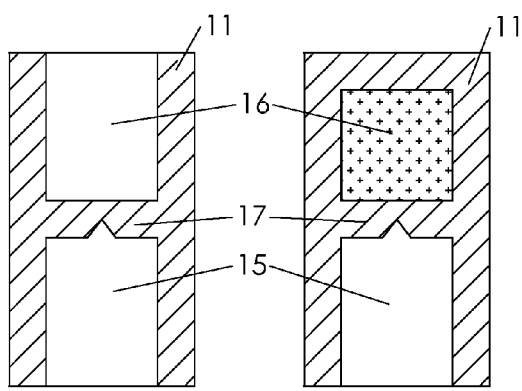
FIG. 25 demonstrates method for fabricating the pouch.

Referring to FIGS. 25a-25d, a method for producing a two compartment package is demonstrated. Referring to FIG. 25a, prior to filling, the seams of the two major walls are welded together except for opening areas which are left open for filling the compartments. The frangible seal 17 is welded usually at a lower temperature than the seam welding. FIG. 25b shows how the second compartment 16 filled and sealed. FIG. 25c shows how the package 11 is turned upside down, preparing it for filling the first compartment 15. FIG. 25d shows how the second compartment has been filled and sealed. It will be obvious to those skilled in the art that the package 11 is preferably manufactured as strips articulating numerous packages 11.

Figures 26A, 26B, 26C:
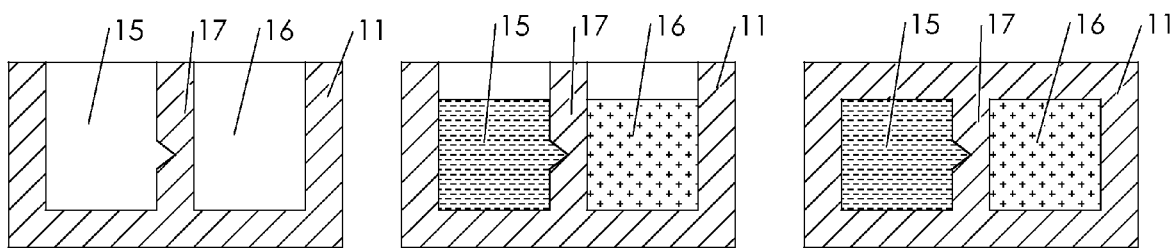
FIG. 26 demonstrates a further method for fabricating the pouch.

FIG. 26 demonstrates a filling from the side. Referring to FIG. 26a, once again most of the contour of the package 11 is sealed prior to filling. FIG. 26b demonstrates the package 11 when both compartments are filled and FIG. 26b demonstrates the package 11 when both compartment are sealed.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

What is claimed:

1. A device for dispensing a dose of a substance to a subject, comprising:
   a. a sealed package including a collapsible compartment containing the substance;
   b. an administration assembly joined to said sealed package for relative movement therewith, said administration assembly including a delivery device movable from a pre-administration position wherein said delivery device is separated from the substance, to a ready position wherein said delivery device is in fluid communication with the substance;
   c. a reinforcement insert joined to a wall of said collapsible compartment to provide a backing for said seal as said delivery device is advanced toward the ready position;
   d. a seal interposed between the administration assembly and the substance; and
   e. at least one compression panel associated with said sealed package and movable into an engaged state wherein said compression panel collapses said compartment to cause said substance to be dispensed through said delivery device.

2. A device according to claim 1 wherein said reinforcement insert is attached to both said coupler and an interior wall surface of said collapsible compartment.

3. A device according to claim 2 wherein said reinforcement insert is snap-fitted to said coupler.

4. A single use dispenser for hypodermic administration of a unit dose of a therapeutic fluid to a subject, comprising:
   a. a hermetically sealed package including a collapsible first compartment containing a first therapeutic substance, said collapsible first compartment comprising a first flexible wall;
   b. a rigid backing supporting said hermetically sealed package to facilitate collapsing of the collapsible first compartment;
   c. an administration assembly associated with said hermetically sealed package, said administration assembly including:
      i. an elongate needle having a piercing end for penetrating the flexible wall of said first compartment, and extending from said piercing end toward a delivery end for administering the therapeutic fluid to the subject; and
      ii. a needle actuator for advancing at least a portion of said needle from a pre-administration position, wherein said piercing end is separated from the flexible wall of said first compartment, towards a ready position to cause said proximal end to breach the integrity of said flexible wall and establish fluid communication between the therapeutic substance and said delivery end.

5. A dispenser according to claim 4 comprising a coupler attached to said rigid backing, said coupler configured to removably attach said administration assembly.

6. A dispenser according to claim 5 including a gasket seal interposed between said coupler and the hermetically sealed package.

7. A dispenser according to claim 6 including a reinforcement insert joined to the hermetically sealed package to provide a backing for said gasket seal as said needle is advanced toward the ready position.

8. A dispenser according to claim 7 wherein said collapsible first compartment comprises a multi-layered flexible wall, and wherein said gasket seal is interposed between layers of said flexible wall.

9. A dispenser according to claim 4 wherein said administration assembly includes a hub carrying said needle, said hub frictionally captured within said coupler.

10. A dispenser according to claim 9 wherein said hub is threadedly attached to said coupler such that rotation of said hub relative to said coupler advances said needle from the pre-administration position toward the ready position.

11. A dispenser according to claim 4 including a collapsible second compartment containing a second therapeutic substance, said collapsible first compartment comprising an associated second flexible wall.

12. A dispenser according to claim 11 including a frangible seal disposed between said first and second compartments, and wherein said rigid backing is movably attached relative to the first and second compartments between a flattened state and folded state wherein said rigid backing collapses said second compartment to cause said frangible seal to rupture such that said first and second therapeutic substances are merged.

13. A dispenser according to claim 4 including at least one compression panel associated with said sealed package and movable into an engaged state wherein said compression panel collapses said first collapsible compartment to cause said therapeutic substance to be dispensed through said needle.

14. A dispenser according to claim 13 wherein said compression panel protects said needle when the needle is in the pre-administration position.

15. A dispenser according to claim 13 wherein said compression panel is movable beyond the engaged state to damage, and prevent further use of, said needle.

16. A dispenser according to claim 13 wherein said rigid backing defines said compression panel.

* * * * *